US012669228B1

(12) United States Patent
Li

(10) Patent No.: US 12,669,228 B1
(45) Date of Patent: Jun. 30, 2026

(54) SCENTED ELECTRONIC CANDLE DEVICE

(71) Applicant: L&L Candle Company, LLC, Brea, CA (US)

(72) Inventor: Xiaofeng Li, Shenzhen (CN)

(73) Assignee: L&L Candle Company, LLC, Brea, CA (US)

( * ) Notice: Subject to any disclaimer, the term of this patent is extended or adjusted under 35 U.S.C. 154(b) by 0 days.

(21) Appl. No.: 19/092,559

(22) Filed: Mar. 27, 2025

(51) Int. Cl.
F21S 10/04 (2006.01)
A61L 9/14 (2006.01)
F21W 121/00 (2006.01)

(52) U.S. Cl.
CPC .............. F21S 10/046 (2013.01); A61L 9/14 (2013.01); *A61L 2209/12* (2013.01); *F21W 2121/00* (2013.01)

(58) Field of Classification Search
CPC ................................ F21S 10/046; F21S 6/001
See application file for complete search history.

(56) References Cited

U.S. PATENT DOCUMENTS

| | | | |
|---|---|---|---|
| 5,622,424 | A | 4/1997 | Brady |
| 9,810,388 | B1 | 11/2017 | Li |
| 10,010,640 | B1 * | 7/2018 | Li ............................ F21S 9/02 |
| 10,251,967 | B1 | 4/2019 | Wang |
| 11,484,617 | B2 | 11/2022 | Li |
| 2005/0169666 | A1 | 8/2005 | Porchia et al. |
| 2005/0247802 | A1 | 11/2005 | Varanasi et al. |

| | | | |
|---|---|---|---|
| 2007/0253222 | A1 | 11/2007 | Driska et al. |
| 2008/0068822 | A1 | 3/2008 | Spartano et al. |
| 2009/0310374 | A1 | 12/2009 | Lederer |
| 2011/0019422 | A1 | 1/2011 | Schnuckle et al. |
| 2013/0182446 | A1 | 7/2013 | Gourdie et al. |

(Continued)

FOREIGN PATENT DOCUMENTS

| | | |
|---|---|---|
| CA | 2500563 A1 | 4/2004 |
| CN | 109185823 A | 1/2019 |

(Continued)

OTHER PUBLICATIONS

International Search Report and Written Opinion for International Patent Application No. PCT/US2020/064878, mailed Mar. 30, 2021.

(Continued)

*Primary Examiner* — Alexander K Garlen
(74) *Attorney, Agent, or Firm* — Perkins Coie LLP

(57) ABSTRACT

An electronic candle device is described. In one example, the electronic candle device includes a shell comprising a first opening that allows a movable flame piece to at least partially extend outwardly and a second opening that allows dissemination of a fragrance material to an outside environment. The electronic candle device includes a liquid suction channel that draws the fragrance material from the fragrance container and an atomizer that converts the fragrance material from a liquid state into droplets and allows the droplets to reach the second opening for dissemination to the outside environment. The shell includes an open section at a side of the shell extending upward from a bottom of the shell, allowing at least a portion of the fragrance container to be visible from outside and providing an unobstructed space to facilitate insertion or removal of the fragrance container into or from the mounting base.

20 Claims, 12 Drawing Sheets

800

1001
1003A
910
920
930
1023

(56)              References Cited

U.S. PATENT DOCUMENTS

2016/0195257 A1      7/2016  Hsiao
2017/0067608 A1 *    3/2017  Patton ................. F21V 33/0004
2017/0067625 A1      3/2017  Edgar et al.
2017/0167677 A1      6/2017  Patton et al.
2017/0368219 A1 *   12/2017  Li ............................ C11C 5/00
2018/0283634 A1     10/2018  Ding
2018/0292058 A1 *   10/2018  Li ........................... A61L 9/127
2018/0361005 A1     12/2018  Li
2019/0195447 A1 *    6/2019  Wu ........................... B05B 1/14
2019/0275187 A1      9/2019  Hsiao
2019/0275188 A1      9/2019  Hsiao
2020/0114038 A1 *    4/2020  Yuan .................... F21S 10/046
2021/0178003 A1 *    6/2021  Li ......................... F21S 10/046

FOREIGN PATENT DOCUMENTS

KR     10-2005-0057630 A     6/2005
KR     10-2016-0122055 A    10/2016

OTHER PUBLICATIONS

First Examination Report for Australian Patent Application No.
2020404865, mailed May 11, 2023 (5 pages).
Notice of Reasons for Rejections for Japanese Patent Application
No. 2022-533140, mailed May 9, 2023 (17 pages).
Extended European Search Report for European Patent Application
No. 20903530.2, mailed Dec. 12, 2023 (10 pages).
Examiner's Requisition for Canadian Patent Application No. 3,165,331,
mailed Sep. 6, 2023 (4 pages).
Notice of Allowance for Canadian Patent Application No. 3, 165,331,
mailed Aug. 26, 2025 (1 page).

* cited by examiner

SCENTED ELECTRONIC CANDLE DEVICE

TECHNICAL FIELD

The present disclosure relates to electronic lighting technology, and more particularly, to a scented electronic candle device.

BACKGROUND

In home facilities, public restaurants, churches, temples, large theme parks or urban public infrastructures, candles are used to provide lighting and to create ceremonial or romantic atmospheres. However, a conventional candle has a short lifetime and needs to be replaced frequently. Moreover, a potential risk of fire due to the fire flame prevents candles from being widely used.

SUMMARY

The present disclosure relates to scented electronic candles that, among other features and benefits, provide rich visual and olfactory experiences to users.

In one example aspect, an electronic candle is disclosed. The electronic candle device includes a movable flame piece resembling a real flame and a shell comprising a first opening and a second opening on a top section of the shell. The first opening is configured to allow the movable flame piece to at least partially extend outwardly from the top section of the shell, and the second opening is configured to allow dissemination of a fragrance material to an outside environment of the electronic candle device. The electronic candle device includes one or more light-emitting elements located inside the shell and configured to illuminate the moveable flame element, a mounting base positioned below the moveable flame element, a fragrance container removably coupled to the mounting base and configured to store the fragrance material, and a liquid suction channel. A first end of the liquid suction channel protrudes from the fragrance container. A second end of the liquid suction channel is positioned within the fragrance container and configured to draw the fragrance material from the fragrance container. The electronic candle device includes an atomizer positioned inside the shell and coupled to the first end of the liquid suction channel. The atomizer is configured to convert the fragrance material from a liquid state into droplets. The atomizer is coupled to the second opening to allow the droplets to reach the second opening for dissemination to the outside environment. The shell includes an open section at a side of the shell extending upward from a bottom of the shell. The open section is configured to allow at least a portion of the fragrance container to be visible from an outside of the electronic candle device when the fragrance container is coupled to the mounting base. The open section provides an unobstructed space on one side of the mounting base to facilitate insertion or removal of the fragrance container into or from the mounting base.

These, and other, aspects are described in the present document.

DETAILED DESCRIPTION

In order to facilitate the understanding of the features and advantages of the disclosed technology, the present disclosure will be explained with reference to the example figures and embodiments. It is to be noted here that the embodiments and features can be combined with each other, provided that they do not conflict. The scope of the present disclosure is not limited to the embodiments disclosed below.

With the development of new technologies, electronic candles now can provide illumination similar to real candles and also possess aesthetic and decorative qualities, which has let to their wide-ranging uses in hotels, churches and homes. In particular, scented electronic candles, configured to release various types of fragrances while emitting light, provide a combination of aromatherapy and rich visual experiences for users. This patent document discloses techniques that can be implemented in various embodiments to provide scented electronic candles that operate effectively and safely in diffusing fragrances.

Figure 1:
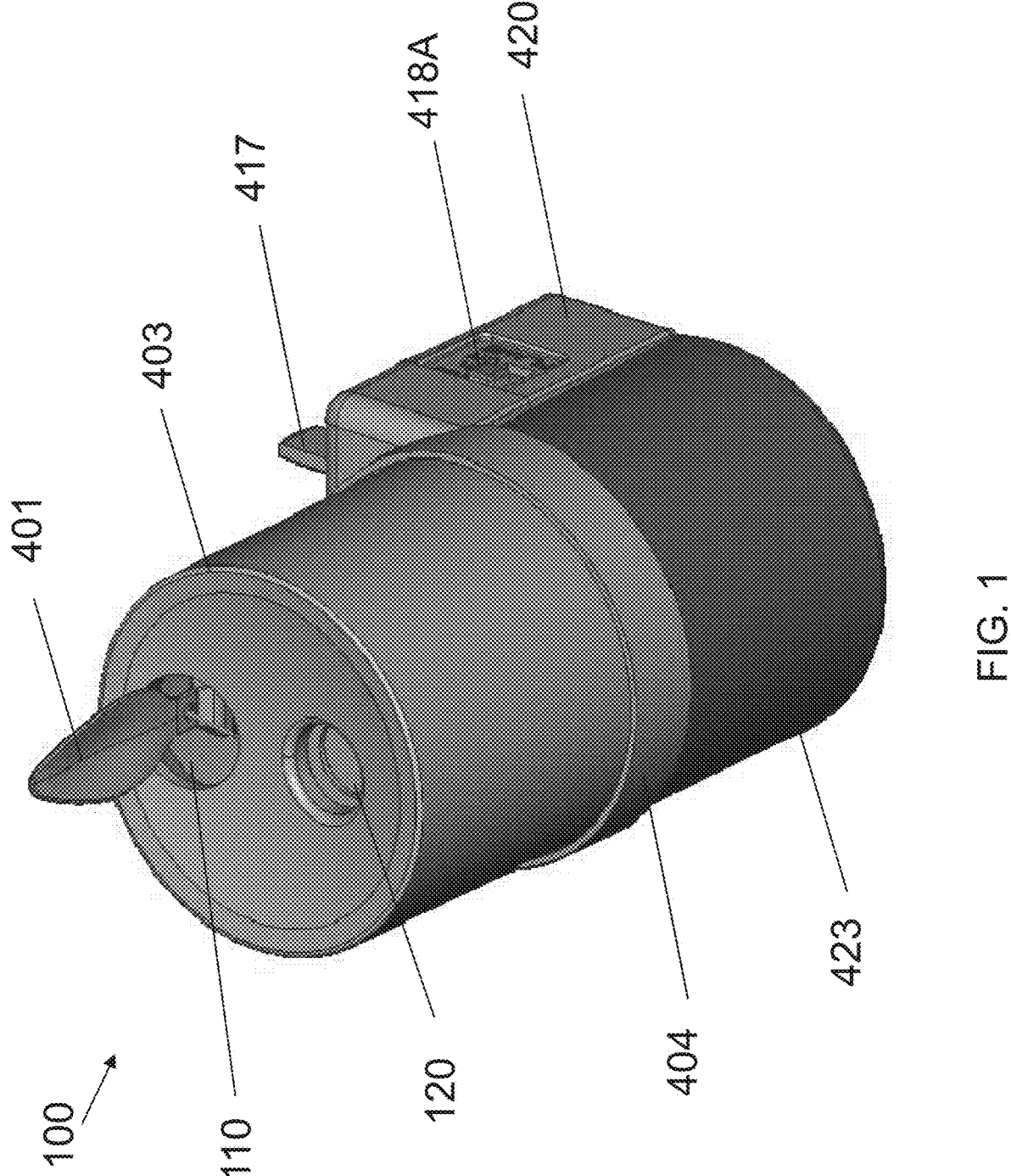
FIG. 1 illustrates a perspective view of an example electronic candle device in accordance with an embodiment of the present disclosure.

FIG. 1 illustrates a perspective view of an electronic candle device 100 in accordance with an embodiment of the present disclosure. As shown, the electronic candle device 100 includes a flame element 401 and a shell 403. The flame element 401 can be partly or completely positioned outside the shell 403. The flame element 401 has a shape of a real flame. The flame element 401 can be a fixed element or a movable element that can swing freely to mimic the flickering movement of a real flame.

The shell 403 can be made of wax to simulate a real candle or any other suitable materials, such as plastic, paraffin, glass, metal, ceramic, crystal, polymers, or any combination thereof. At least a portion of the shell 403 has a cylindrical structure to mimic a real candle. The shell 403 is installed on a mounting base 420, which is coupled to a fragrance container 423. In some examples, the shell 403 covers at least a portion of the mounting base 420 that is positioned below the flame element 401. The shell 403 includes a first opening 110 and a second opening 120 on a top section of the shell 403. The first opening 110 allows the flame element 401 to partially or completely extend outwardly from the top section of the shell 403. The second opening 120 allows dissemination of a fragrance material to an outside environment of the electronic candle device 100. In this way, the fragrance communication path to the outside environment is separated from the first opening 110 associated with the protruding flame element 401, which enables more efficient dissemination of the fragrance, and avoids contamination or discoloration of the flame element 401 even over an extended period of use of the electronic candle device 100. In some embodiments, the first opening 110, the second opening 120, and/or the top section of the shell 403 are circular in shape. The example configuration of FIG. 1 illustrates a single opening (i.e., the second opening 120)—having a diameter that is approximately 10 millimeters (mm) in length or 22.7% of the diameter of the top section of the shell 403—which enables the fragrance to be readily disseminated to the outside environment. In some examples, the diameter of the first opening 110 is approximately 13 mm, and the diameter of the top section of the shell 403 is approximately 44 mm. In some examples, the diameter of the second opening 120 is at least 20% of the diameter of the top section of the shell 403.

The electronic candle device 100 includes a fragrance container 423 that may store the fragrance material in a liquid state for the electronic candle device 100 to disseminate fragrance. Alternatively, or in addition, the fragrance container 423 may store water for the electronic candle device 100 to operate in a humidification mode. In some embodiments, the fragrance material may be stored in the fragrance container 423 as a gas. As shown in FIG. 1, the fragrance container 423 is not transparent and may have a color. In some examples, at least a portion of the fragrance container 423 is transparent or semi-transparent, allowing an interior of the fragrance container 423 to be viewed from outside of the electronic candle device 100. The transparency enables the user to see when the fragrance material has been used up or is close to being depleted.

The electronic candle device 100 includes a collar 404 that is detachably installed on the shell 403, the mounting base 420, or both. In some embodiments, the collar 404 can be positioned to hide the connection between the shell 403 and the mounting base 420. For example, the collar 404 can be positioned close to a lower part of the shell 403 and a top part of the mounting base 420 (i.e., the top base to be discussed in greater details below). The collar 404 can be installed onto the shell 403 or the mounting base 420 via a fastening mechanism (e.g., snap clips or buckles). In some embodiments, the collar 404 can include a printed logo or brand.

The electronic candle device 100 includes a power plug assembly 417. The power plug assembly 417 can include one or more adaptors to adapt to universal interchangeable plugs, suitable for international usage. As shown, the power plug assembly 417 is coupled to the mounting base 420. In some examples, the power plug assembly 417 is coupled to the mounting base 420 in a similar manner as mounting a screw (e.g., by rotating the power plug assembly 417). The power plug assembly 417 is connected to a control circuit (e.g., the control circuit 416 in FIGS. 5 and 6). When the power plug assembly 417 is plugged into a power supply, the electronic candle device 100 is provided a power to operate. In some embodiments, the electronic candle device 100 functions as a night light to provide aroma as well as soft lighting overnight.

Figure 2:
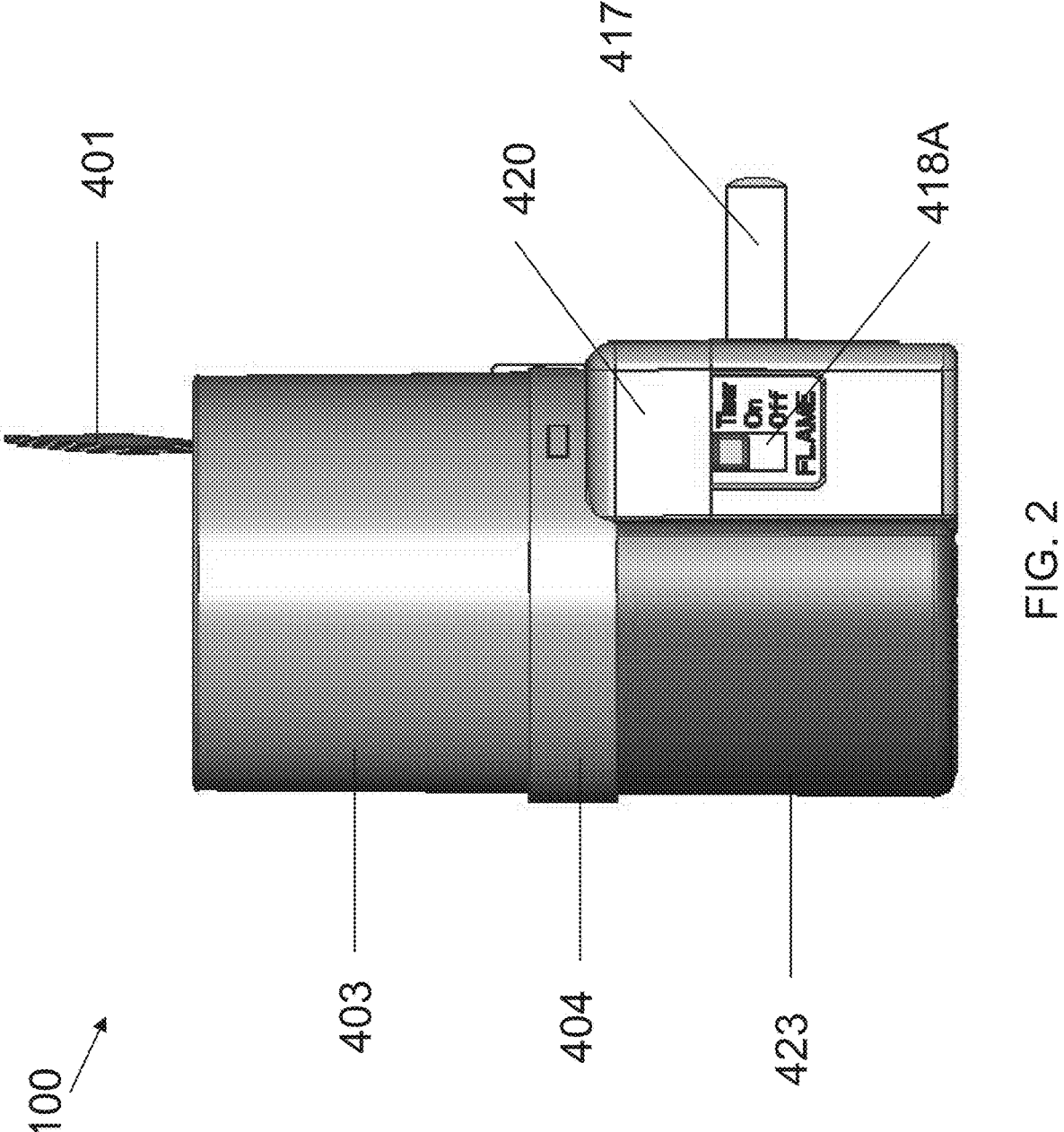
FIG. 2 illustrates a side view of an example electronic candle device in accordance with an embodiment of the present disclosure.
Figure 3:
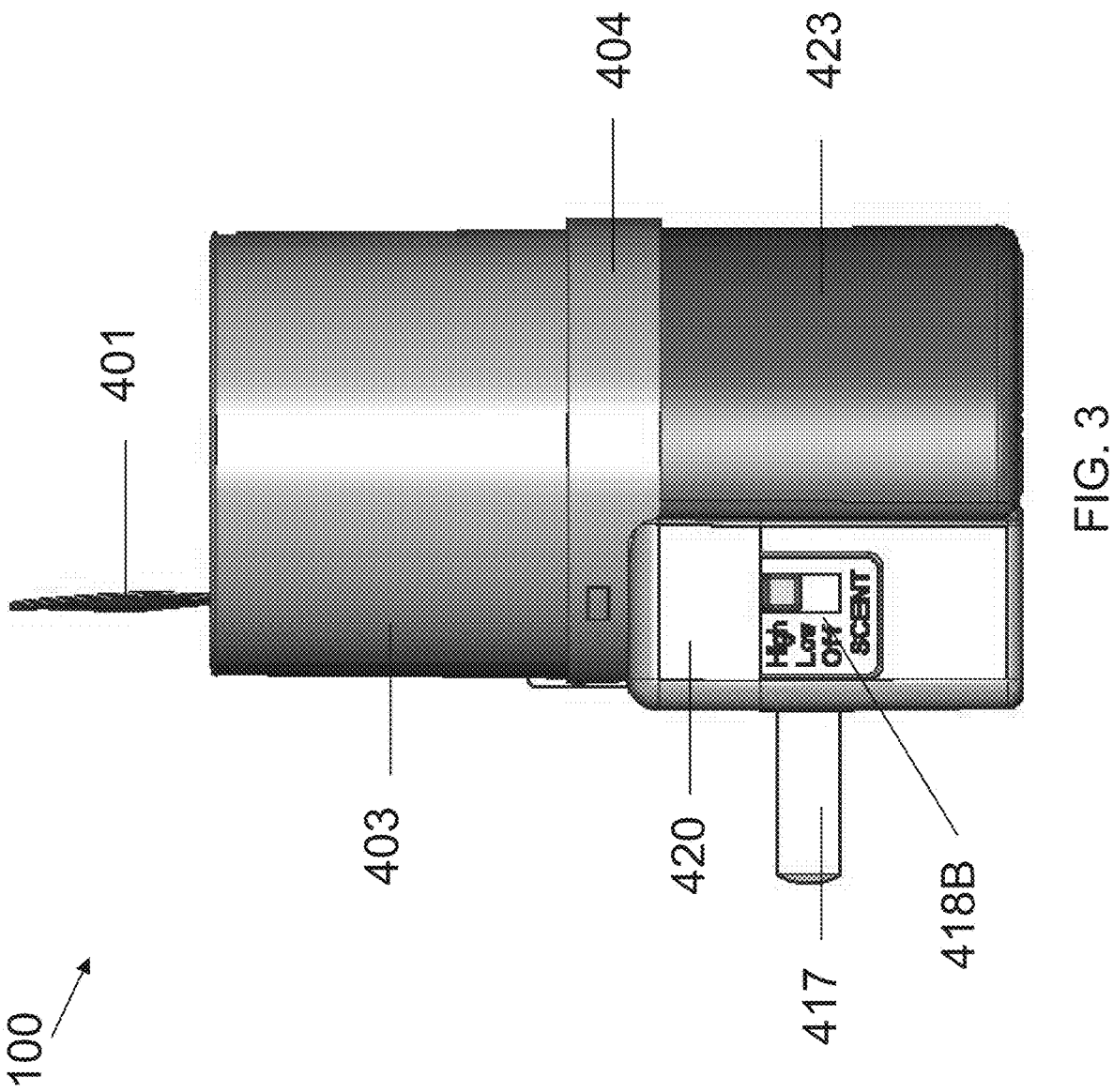
FIG. 3 illustrates another side view of an example electronic candle device in accordance with an embodiment of the present disclosure.

The electronic candle device 100 may include one or more toggle switches 418A, 418B to control operations of the electronic candle device 100. For example, the electronic candle device 100 may include a first toggle switch 418A and a second toggle switch 418B as shown in the perspective view in FIG. 1 and in the side views in FIGS. 2-3. The first toggle switch 418A and the second toggle switch 418B are coupled to different sides of the mounting base 420. The first toggle switch 418A can cause the flame element 401 to be illuminated continuously at a first position ("ON"), to not be illuminated at a second position ("OFF"), or to be illuminated in a timer mode at a third position ("Timer"). As discussed in greater details below related to FIGS. 4 and 6, the electronic candle device 100 includes one or more light-emitting elements 412 that illuminates lights on at least an upper portion of the flame element 401 to simulate a real flame when the toggle switch 418A is at either the first position ("ON") or the third position ("Timer"). Specifically, in the timer mode, the one or more light-emitting elements 412 may continuously illuminate the flame element 401 for a first period of time before stopping for a second period of time. This cycle then repeats. In some examples, the first period of time and the second period of time sum to 24 hours. For example, the first period of time may be 4 hours, 5 hours, 6 hours, 7 hours, 8 hours, 9 hours, or 10 hours. Accordingly, the second period of time may be 20 hours, 19 hours, 18 hours, 17 hours, 16 hours, 15 hours, or 14 hours, respectively.

The second toggle switch 418B can cause no dissemination of fragrance out of the electronic candle device 100 at a first position ("OFF"), cause disseminations of fragrance out of the electronic candle device 100 at a lower frequency at a second position ("Low"), or cause disseminations of fragrance out of the electronic candle device 100 at a high frequency at a third position ("High"). As discussed in greater details below related to FIGS. 4 and 6, the electronic candle device 100 includes an atomizer 407 that converts the fragrance material from a liquid state to droplets to generate a fragrance spray through the second opening 120 located on the top section of the shell 403 when the second toggle switch 418B is at either the second position ("Low") or the third position ("High"). Specifically, when the second toggle switch 418B is at the second position ("Low"), the atomizer 407 generates a fragrance spray to disseminate the fragrance out of the electronic candle device 100 at a first time interval. Examples of the first time interval include 15 minutes, 16 minutes, 17 minutes, etc. When the second toggle switch 413B is at the third position ("High"), the atomizer 407 generates a fragrance spray to disseminate the fragrance out of the electronic candle device at a second time interval. The second time interval is shorter than the first time interval. Examples of the second time interval include 3 minutes, 4 minutes, 5 minutes, etc. In addition or alternatively, the atomizer 407 operates in a timer mode by default when the second toggle switch 418B is at the second position ("Low") or the third position ("High"). For example, the atomizer 407 may generate a fragrance spray at a time interview (e.g., the first time interval at the second position or the second time interval at the third position) for a first period of time (for example, 8 hours) before stopping operating for a second period of time (for example, 16 hours). Then the cycle repeats.

Figure 4:
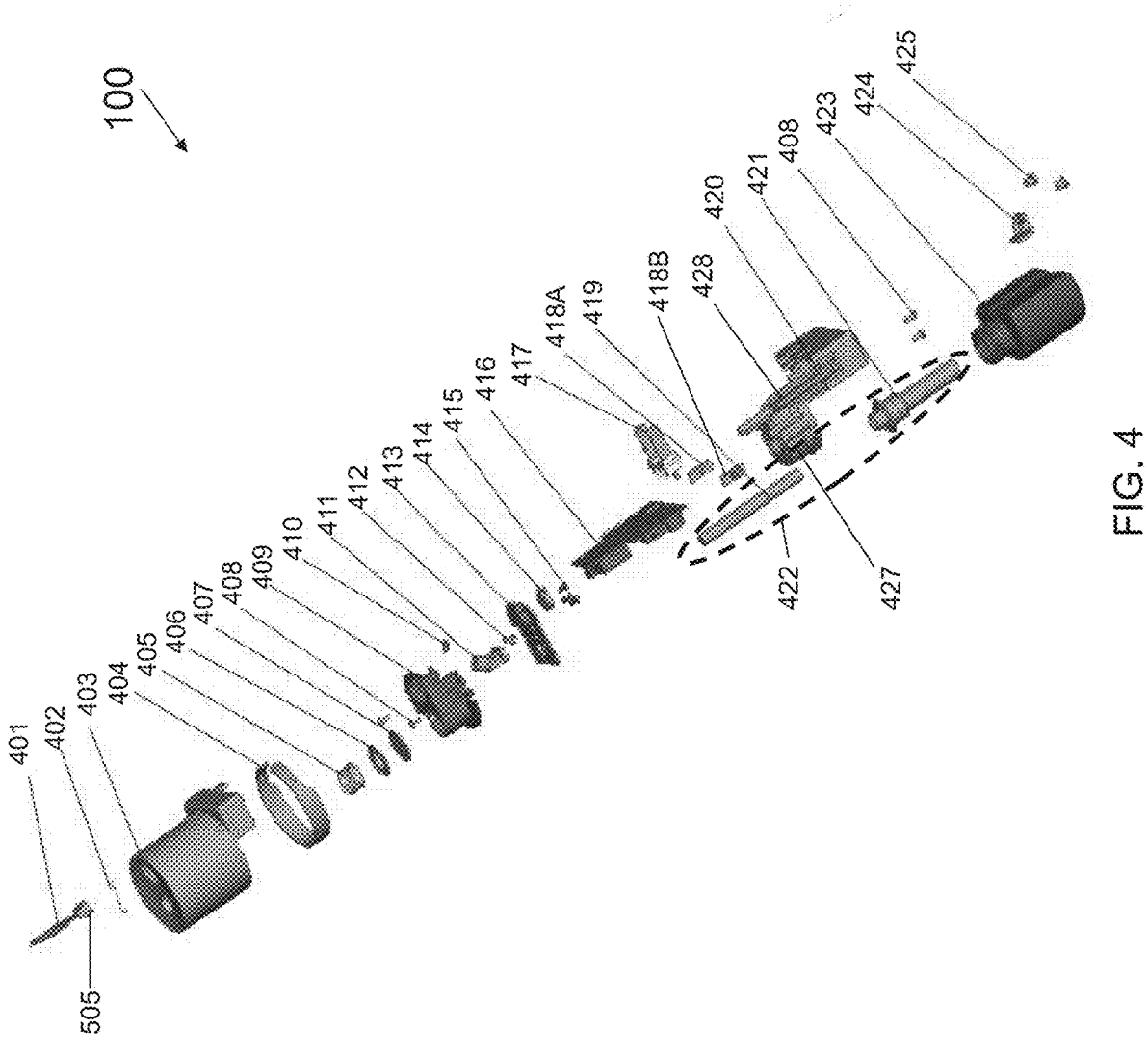
FIG. 4 illustrates an exploded view of an example electronic candle device in accordance with an embodiment of the present disclosure.

FIG. 4 illustrates an exposed view of the electronic candle device 100 in accordance with an embodiment of the present disclosure. As shown, the electronic candle device 100 includes the flame element 401 that includes a magnet 505 at the lower end of the flame element 401. The electronic candle device 100 further includes a wire 402, the shell 403, the collar 404, a spring 405, a ring gasket 406, the atomizer 407, screws 408, a support structure 409, a lens 410, a light-emitting element holder 411, one or more light-emitting elements 412, a coil holder 413, a magnetic coil 414, a control circuit 416, the power plug assembly 417, the first toggle switch 418A, the second toggle switch 418B, a liquid suction channel 422 including an absorptive section 419 and a housing 421, the mounting base 420, the fragrance container 423, a transparent window 424, and two plugs 425.

As shown, the mounting base 420 includes a top base 427 and a main body 428. In some examples, the bottom of the top base 427 is perpendicular with a sidewall of the main body 428 to form an inverted L shape. In some embodiments, the sidewall of the main body 428 is coupled to the top base 427 and extends vertically downward to the bottom of the mounting base 420. The top base 427 protrudes from one side of the main body 428 to be coupled with the fragrance container 423 such that the fragrance container 423 is arranged side by side with the main body 428. Additionally, or alternatively, the fragrance container 423 can be connected to the main body 428 of the mounting base 420.

The control circuit 416 is coupled to the one or more light-emitting elements 412 and the first toggle switch 418A to control operations of the one or more light-emitting elements 412 according to the respective position selected on the first toggle switch 418A as discussed above. In addition, the control circuit 416 is coupled to the atomizer 407 and the second toggle switch 418B to control operations of the atomizer 407 according to the respective position selected on the second toggle switch 418B as discussed above. In some embodiments, the control circuit 416 is a printing circuit board (PCB).

In some embodiments, the electronic candle device 100 includes a motion or acoustic sensor (e.g., a microphone) that is held in place within the interior thereof. The sensor converts motion and/or acoustic signals into electrical signals that are provided to the control circuit 416. For example, a microphone can be positioned closer to the top section of the electronic candle device 100 to intercept sound waves that travel into the interior of the electronic candle device 100. The first opening 110 and/or the second opening 120 on the top section of the shell 403 allow the microphone to capture acoustic waves that travel down into the interior of the electronic candle device 100. In this way, when a user blows in the direction of the electronic candle device 100, the blow is captured by the microphone, and the appropriate signals are generated to turn off the electronic candle device 100.

Figure 5:
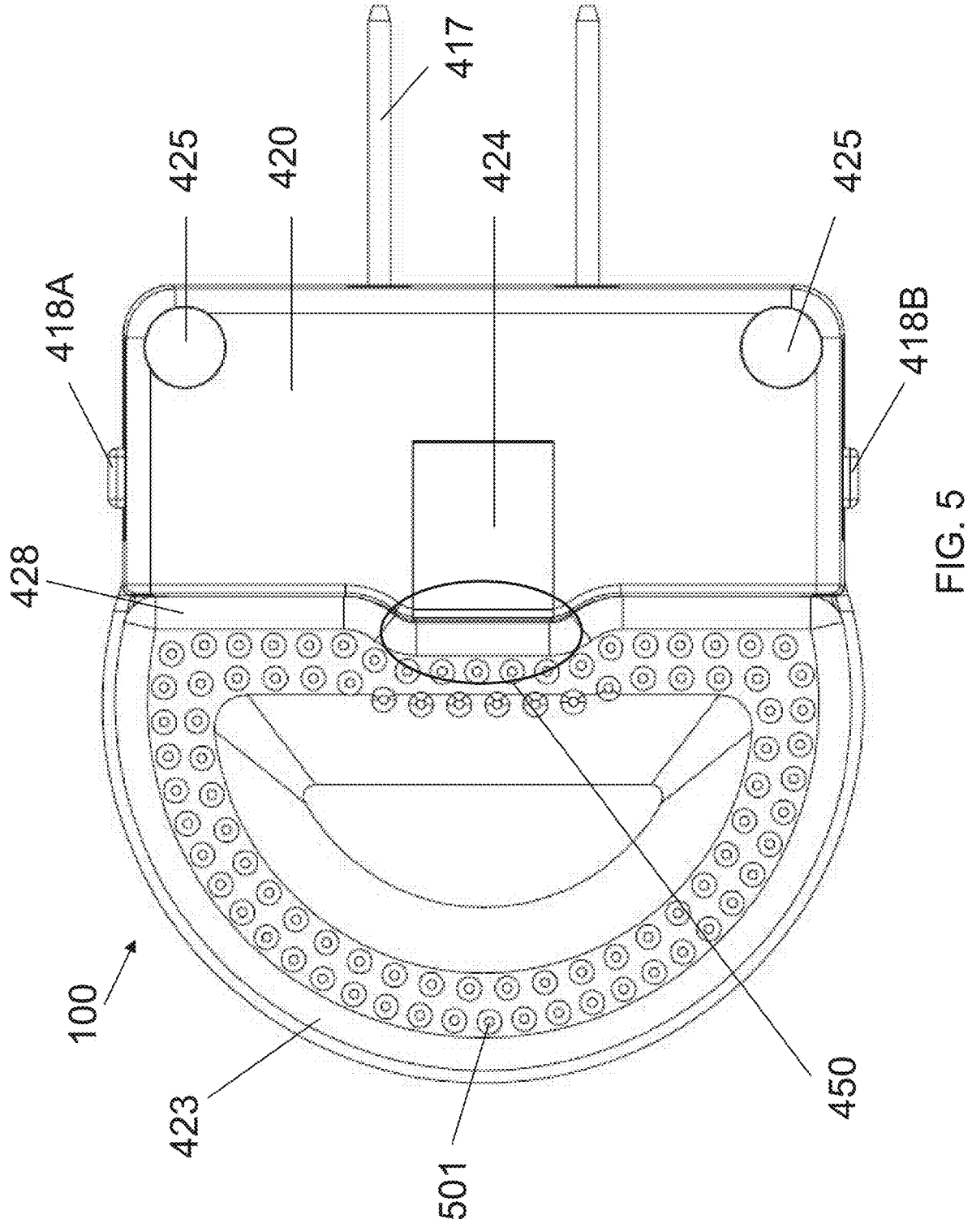
FIG. 5 illustrates a bottom view of an example electronic candle device in accordance with an embodiment of the present disclosure.

FIG. 5 illustrates a bottom view of the electronic candle device 100 in accordance with an embodiment of the present disclosure. As shown, the fragrance container 423 is coupled to the mounting base 420. In some embodiments, the main body 428 of the mounting base 420 has a limiting protrusion 450 positioned on, and extending outward from, at least a section of the sidewall facing the fragrance container 423. The part of the fragrance container 423 facing the main body 428 includes a groove that matches the limiting protrusion 450. Alternatively, or in addition, the main body 428 of the mounting base 420 has a limiting groove on the sidewall while the part of the fragrance container 423 facing the main body 428 includes a protrusion that matches the limiting groove. The limiting protrusion 450/groove and the corresponding groove/protrusion ensure that the fragrance container 423 is securely connected to the mounting base 420 and prevent the fragrance container 423 from shifting left or right from the mounting base 420. As shown in FIG. 5, in addition to the power plug assembly 417 coupled to the mounting base 420, the mounting base 420 includes two holes at the two corners that are filled by two plugs 425, respectively. The mounting base 420 also includes the transparent window 424, which will be discussed in greater detail below. A plurality of small circular features 501 are added at the bottom of the fragrance container 423 to provide stability and improve contact with the surface upon which the electronic candle device 100 is positioned.

Figure 6:
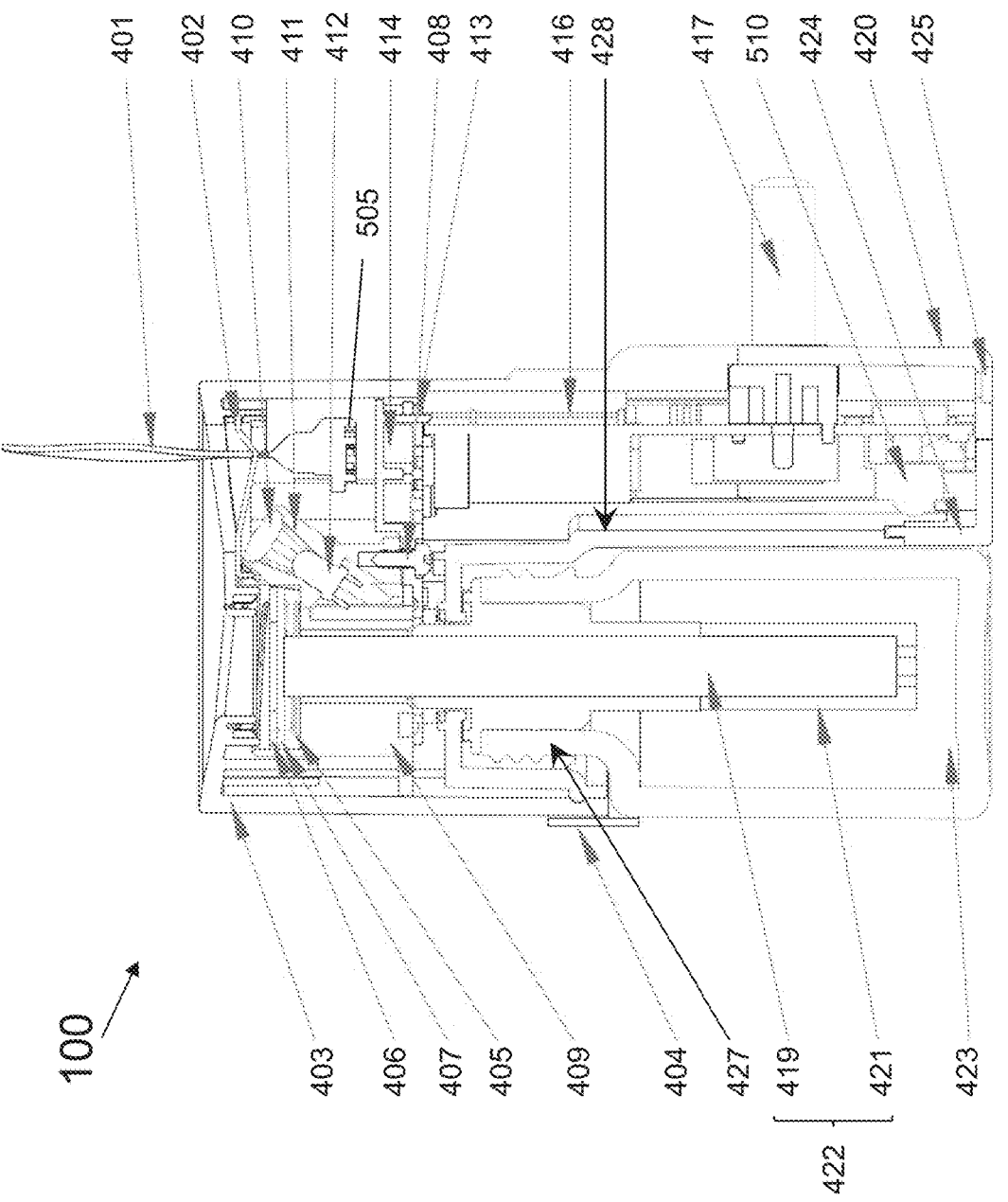
FIG. 6 illustrates a cross-sectional view of an example electronic candle device in accordance with an embodiment of the present disclosure.

FIG. 6 illustrates a cross-sectional view of the electronic candle device 100 in accordance with an embodiment of the present disclosure. In some embodiments, the flame element 401 can be either fixedly or movably coupled to the wire 402, which is positioned across the first opening 110 to support the flame element 401. For example, this can be achieved by passing the wire through a hole in the flame element 401. In some embodiments, the hole is positioned in the lower half of the flame element 401. Additionally, or alternatively, a hook bracket may be provided in the electronic candle device 100 to support the flame element 401. In some embodiments, the flame element 401 is coupled to the shell 403 near the first opening 110 through a coupler (not shown). In some examples, the coupler has one end that is fixedly coupled to the shell 403 and the other end movably coupled to the flame element 401. In some examples, the coupler has one end that is movably coupled to the shell 403 and the other end fixedly or movably coupled to the flame element 401.

In some embodiments, the flame element 401 includes a magnet 505 at the lower end of the flame element 401. The electronic candle device 100 includes a magnetic coil 414 positioned below the flame element 401. The magnetic coil 414 is coupled to the control circuit 416 to alter the generated magnetic field, thereby driving the movement of the flame element 401 to simulate the movement of a real flame. The magnetic coil 414 can be positioned in the coil holder 413. In some examples, the oil holder 413 is installed on the mounting base 420. In some embodiments, the flame element 401 is driven by an air flow produced by a fan or from the outside of the electronic candle device 100.

The electronic candle device 100 includes one or more light-emitting elements 412 that emit light onto the flame element 401. The one or more light-emitting elements 412 may include one or more light-emitting diodes (LEDs). In some embodiments, the one or more light-emitting elements 412 emit lights of different colors. In some embodiments, the one or more light-emitting elements 412 are coupled to the light-emitting element holder 411 at an upward inclined angle so that the light emitted by the one or more light-emitting elements 412 can illuminate on the upper part of the flame element 401. In some embodiments, at least part of the one or more light-emitting elements 412 is movable with respect to the light-emitting element holder 411 and the flame element 401. The light-emitting element holder 411 provides the lens 410 positioned between the one or more light-emitting elements 412 and the flame element 401 to direct and focus the light emitted from the one or more light-emitting elements 412 to the flame element 401. The angle of the light illuminated by the one or more light-emitting elements 412, the relative movement between the flame element 401 and the one or more light-emitting elements 412, and/or the combination of colors of the lights from the one or more light-emitting elements 412 form an effect that simulates a real flame.

In some embodiments, the top base 427 of the mounting base 420 is formed as a clamp to allow the top end of the fragrance container 423 to be securely clamped to the mounting base 420. In some embodiments, the top base 427 includes a mounting hole into which the top end of the fragrance container 423 is inserted and securely clamped. As shown in FIG. 6, the liquid suction channel 422 is inserted into the fragrance container 423 through the opening of the fragrance container 423. The lower end of the liquid suction channel 422 extends into the fragrance container 423, and the upper end extends outside of the fragrance container 423. The angle of the liquid suction channel 422 with respect to a central axis of the fragrance container 423 can be adjusted. The arrangement of the liquid absorption channel 422 is configured to maximize the amount of fragrance drawn from the fragrance container 423 and to control the direction in which the fragrance is directed from the fragrance container 423.

The liquid suction channel 422 includes the housing 421 and the absorptive section 419 disposed within the housing 421. The absorptive section 419 includes an absorbent material capable of absorbing liquid, such as cotton or woven felt, so as to deliver the fragrance material in the fragrance container 423 from the lower end of the absorptive section 419 to the upper end of the absorptive section 419 due to the capillary action. In some embodiment, the housing 421 includes at least one opening formed on a sidewall of the housing at the lower end of the housing 421. Additionally, or alternatively, the housing 421 includes an opening formed on the bottom of the lower end of the housing 421. The housing 421 is made of waterproof material, such as oiled paper or plastic wrap, to prevent excessive loss of fragrance during movement of the fragrance from the lower end of the absorptive section 419 to the upper end of the absorptive section 419. The absorptive section 419 is at least as long as the housing 421. In some examples, the absorptive section 419 is longer than the housing 421.

The atomizer 407 is positioned in the shell 403 and in proximity to the upper end of the absorptive section 419 of the liquid suction channel 422. In some embodiment, the atomizer 407 is in contact with the upper end of the absorptive section 419. As shown in FIG. 6, the spring 405 is positioned beneath the atomizer 407 inside the shell 403 with one end of the spring 405 attached to the support structure 409 and a second end of the spring coupled to the atomizer 407. The ring gasket 406 is positioned above the atomizer 407 and between the atomizer 407 and the shell 403.

In some embodiments, the atomizer 407 has one side above and supported by the support structure 409 and the other side in touch with the ring gasket 406 that is positioned above the atomizer 407. Additionally, the spring 405 is positioned above the ring gasket 406 with one end of the spring 405 coupled to the shell 403 (e.g., beneath the second opening 120) and the other end of the spring 405 coupled to the ring gasket 406. By placing the atomizer 407 between the spring 405 and the ring gasket 406, the position of the atomizer 407 is secured inside the shell 403.

The atomizer 407 is coupled to the control circuit 416 and can convert the fragrance material, which is delivered from the lower end to the upper end of the absorptive section 419, from a liquid state into droplets. This generates a spray that is disseminated into the outside environment through the second opening 120 on the top section of the shell 403. In some embodiments, the atomizer 407 includes a plurality of holes in the center area that allows the droplets to pass through the atomizer 407. In some embodiments, the upper end of the absorptive section 419 is in contact with at least a portion of the holes in the atomizer 407. In some examples, the atomizer 407 is an ultrasonic atomizer that includes an ultrasonic transducer and a vibrating surface. The ultrasonic transducer is coupled to a power source (e.g., a battery, an electrical outlet, etc.) and can convert an electrical energy into sound waves. The vibrating surface can generate a spray or mist from a liquid by vibrating at ultrasonic frequencies of the sound waves when activated by a control circuit (e.g., the control circuit 416). In some examples, the atomizer 407 is a heat-based atomizer that includes a heating coil and an airflow system both connected to a power source (e.g., a battery, an electrical outlet, etc.). The heating coil can heat a liquid to create vapor when activated by a control circuit (e.g., the control circuit 416). The airflow system can flow air to the vapor to create a spray or mist.

The transparent window 424, which has an L shape as shown in FIG. 4 and FIG. 6, is positioned at the bottom of the main body 428 of the mounting base 420 and covers an L shaped open bottom section of the main body 428. The transparent window 424 is positioned at the bottom center of sidewall of the main body 428 of the mounting base 420. In some examples, the transparent window 424 is made of plastic or any other suitable material that allows light to pass through as discussed in greater details below.

In some embodiment, the electronic candle device 100 includes an indicator light emitter 510 behind a part of the transparent window 424 facing the fragrance container 423. In some examples, the indicator light emitter 510 may be positioned behind the bottom center of the fragrance container 423. The indicator light emitter 510 can illuminate the fragrance container 423 through the transparent window 424 to cause the remaining fragrance material in the fragrance container 423 to be visible. For example, the fragrance container 423 can be made of transparent or semi-transparent materials. The indicator light emitter 510 is connected to the control circuit 416 and configured to illuminate the body of the fragrance container 423 such that the amount of fragrance material remained in the fragrance container 423 is visible to the user of the electronic candle device 100. In some embodiments, the indicator light emitter 510 may include one or more LEDs.

Figure 7:
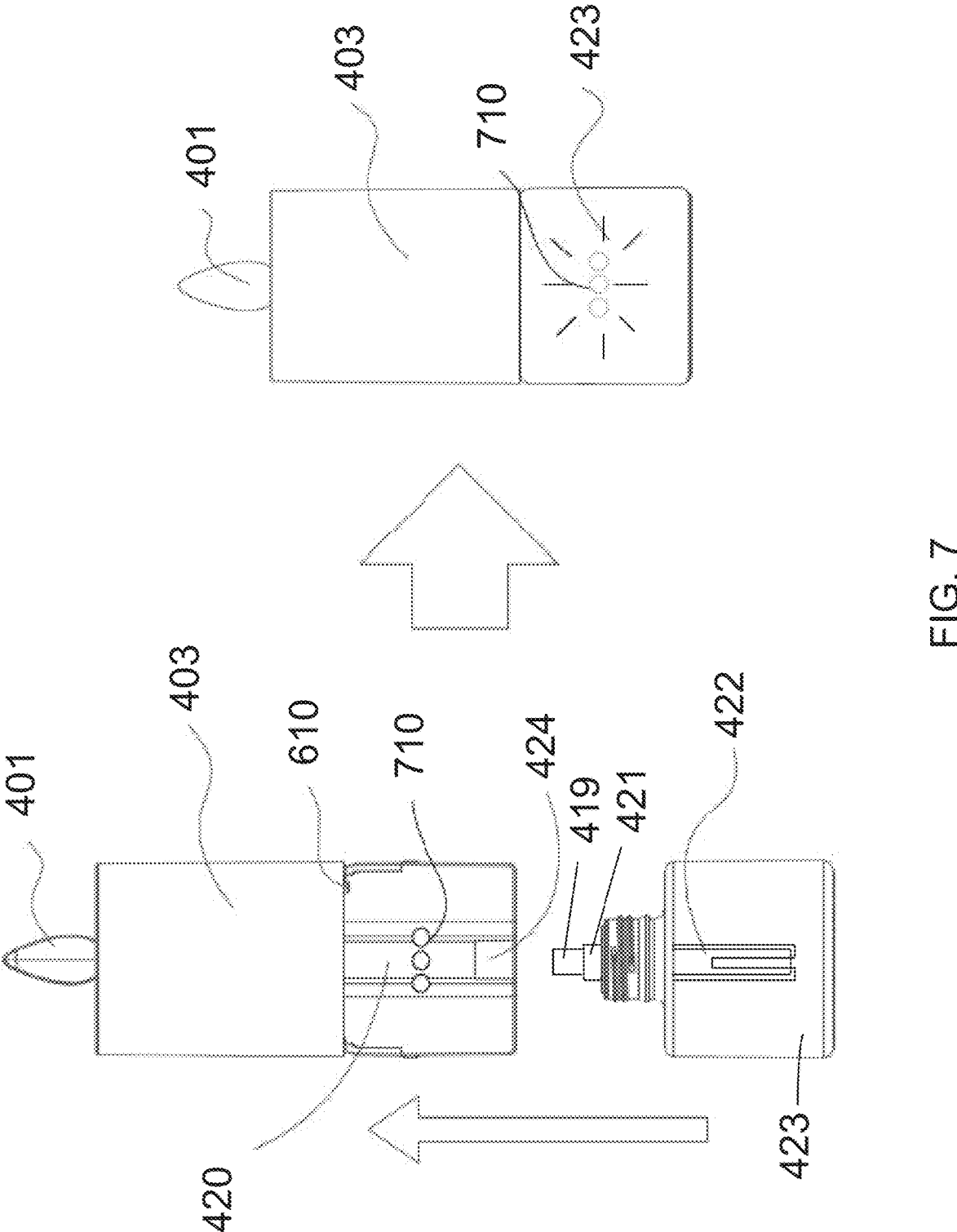
FIG. 7 illustrates an example process of installing an example electronic candle device in accordance with an embodiment of the present disclosure.

FIG. 7 illustrates a process of installing the fragrance container 423 into the mounting base 420 in accordance with an embodiment of the present disclosure. As shown, the fragrance container 423 can be pushed into the top base 427 of the mounting base 420 (not shown) along the sidewall of the main body 428 of the mounting base 420 until it snaps into a slot of the top base 427. If a user wants to remove the fragrance container 423 from the mounting base 420, the user may touch and press the bottom of the fragrance container 423 to cause the fragrance container 423 to disengage from the slot in the top base 427 of the mounting base 420. In some embodiments, the fragrance container 423 can be snapped into the slot in the top base 427 through a buckle. When the fragrance container 423 needs to be replaced or refilled, the fragrance container 423 may be rotated at an angle such that the fragrance container 423 that is installed with the mounting base 420 disengages from slot in the top base 427 of the mounting base 420.

As shown in FIG. 7, the electronic candle device 100 includes a detection unit 610 and one or more light sources 710 (e.g., one or more LEDs) on the mounting base 620. The detection unit 610 and the one or more light sources 710 are connected to the control circuit 416. The one or more light sources 710 are positioned behind the fragrance container 423 when the fragrance container 423 is installed to the mounting base 420. The detection unit 610 can detect whether the fragrance container 423 is properly installed to the mounting base 420. In some embodiments, the detection unit 610 is triggered to generate a signal to the control circuit 416 when it detects that the fragrance container 423 is properly installed to the mounting base 420. Upon receipt of the signal, the control circuit 416 causes the one or more light sources 710 to emit light of a specific color or change the color of the light emitted by the one or more light sources 710 from behind the fragrance container 423 (e.g., transparent/translucent glass or plastic bottle) according to the settings (such as user preferences or time of the day).

The detection unit 610 may include one or more types of sensor devices, such as a photoelectric sensor, a trigger switch, an optical switch, an electrical switch, or a magnetic switch, and may generate one or more types of signals, such as an optical signal, an electrical signal, or a magnetic signal when it is triggered. In some embodiments, the detection unit 610 includes a trigger switch located on the sidewall of the main body 428 of the mounting base 420 and triggered when the electronic candle device 100 is installed to the mounting base 420 and touches the trigger switch on the sidewall of the main body 428 of the mounting base 420. In some embodiments, the trigger switch can be a touch switch that can be turned on or off when it is in contact with the fragrance container 423. For example, the touch switch may be positioned in the slot of the top base 427 and is trigger when the fragrance container 423 is properly installed to the mounting base 420 and the absorptive section 419 or the housing 421 of the liquid suction channel 422 touches the touch switch in the slot of the top base 427.

Figure 8:
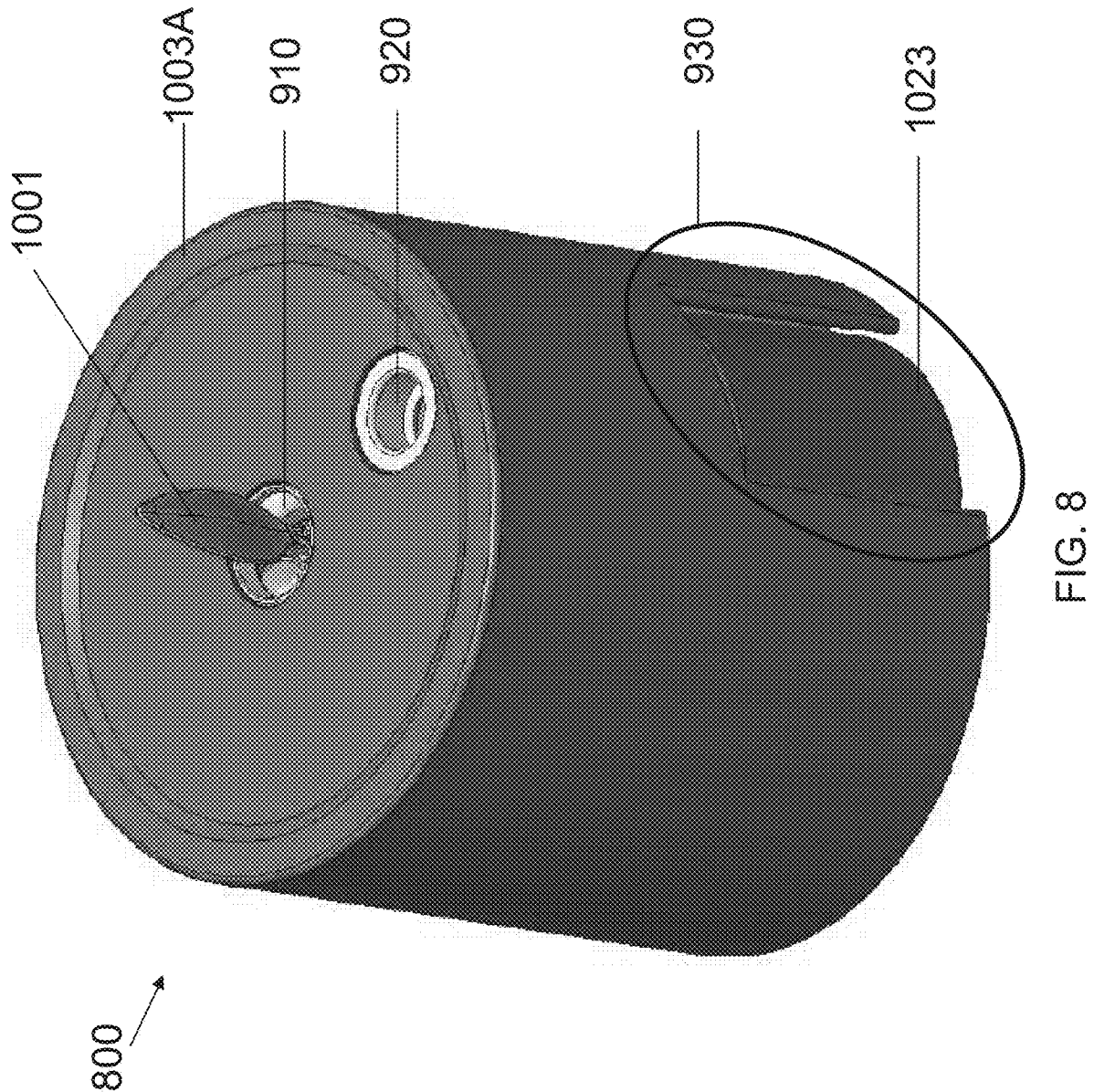
FIG. 8 illustrates a perspective view of an example electronic candle device in accordance with an embodiment of the present disclosure.

FIG. 8 illustrates a perspective view of another electronic candle device 800 in accordance with an embodiment of the present disclosure. As shown, the electronic candle device 800 includes a flame element 1001 and an outer shell 1003A. The flame element 1001 can be partly or completely positioned outside the outer shell 1003A. The flame element 1001 has a shape of a real flame. The flame element 1001 can be a fixed element or a movable element that can swing freely to mimic the flickering movement of a real flame. In some embodiment, the flame element 1001 is substantially similar to the flame element 401.

The outer shell 1003A can be made of wax to simulate a real candle or any other suitable materials, such as plastic, paraffin, glass, metal, ceramic, crystal, polymers, or any combination thereof. The outer shell 1003A has a cylindrical structure. As shown, the outer shell 1003A includes an open section 930 at a side of the outer shell 1003A extending upward from the bottom of the outer shell 1003A. The outer shell 1003A includes a first opening 910 and a second opening 920 on a top section of the outer shell 1003A. The first opening 910 allows the flame element 1001 to partially or completely extend outwardly from the top section of the outer shell 1003A. The second opening 920 allows dissemination of a fragrance material to an ambient environment of the electronic candle device 800. In this way, the fragrance communication path to the outside environment is separated from the first opening 910 associated with the protruding flame element 1001, which enables more efficient dissemination of the fragrance, and avoids contamination or discoloration of the flame element 1001 even over an extended period of use of the electronic candle device 800. In some embodiments, the first opening 910, the second opening 920, and/or the top section of the outer shell 1003A are circular in shape. The example configuration of FIG. 8 illustrates a single opening (i.e., the second opening 920)—having a diameter that is approximately 15 millimeters (mm) in length or 18.8% of the diameter of the top section of the outer shell 1003A—which enables the fragrance to be readily disseminated to the outside environment. In some examples, the diameter of the first opening 910 is approximately 15 mm, and the diameter of the top section of the outer shell 1003A is approximately 80 mm. In some examples, the diameter of the second opening 920 is at least 18% of the diameter of the top section of the outer shell 1003A.

The electronic candle device 800 includes a fragrance container 1023. In some embodiments, the fragrance container 1023 is substantially similar in shape and size to the fragrance container 423. The fragrance container 1023 may store the fragrance material in a liquid state for the electronic candle device 800 to disseminate fragrance. Alternatively, or in addition, the fragrance container 1023 may store water for the electronic candle device 800 to operate in a humidification mode. In some embodiments, the fragrance material may be stored in the fragrance container 1023 as a gas. As shown in FIG. 8, the fragrance container 1023 is not transparent and may have a color. In some examples, at least a portion of the fragrance container 1023 is transparent or semi-transparent, allowing an interior of the fragrance container 1023 to be viewed from outside of the electronic candle device 800 through the open section 930 of the outer shell 1003A. The transparency enables the user to see when the fragrance material has been used up or is close to being depleted.

Figure 9:
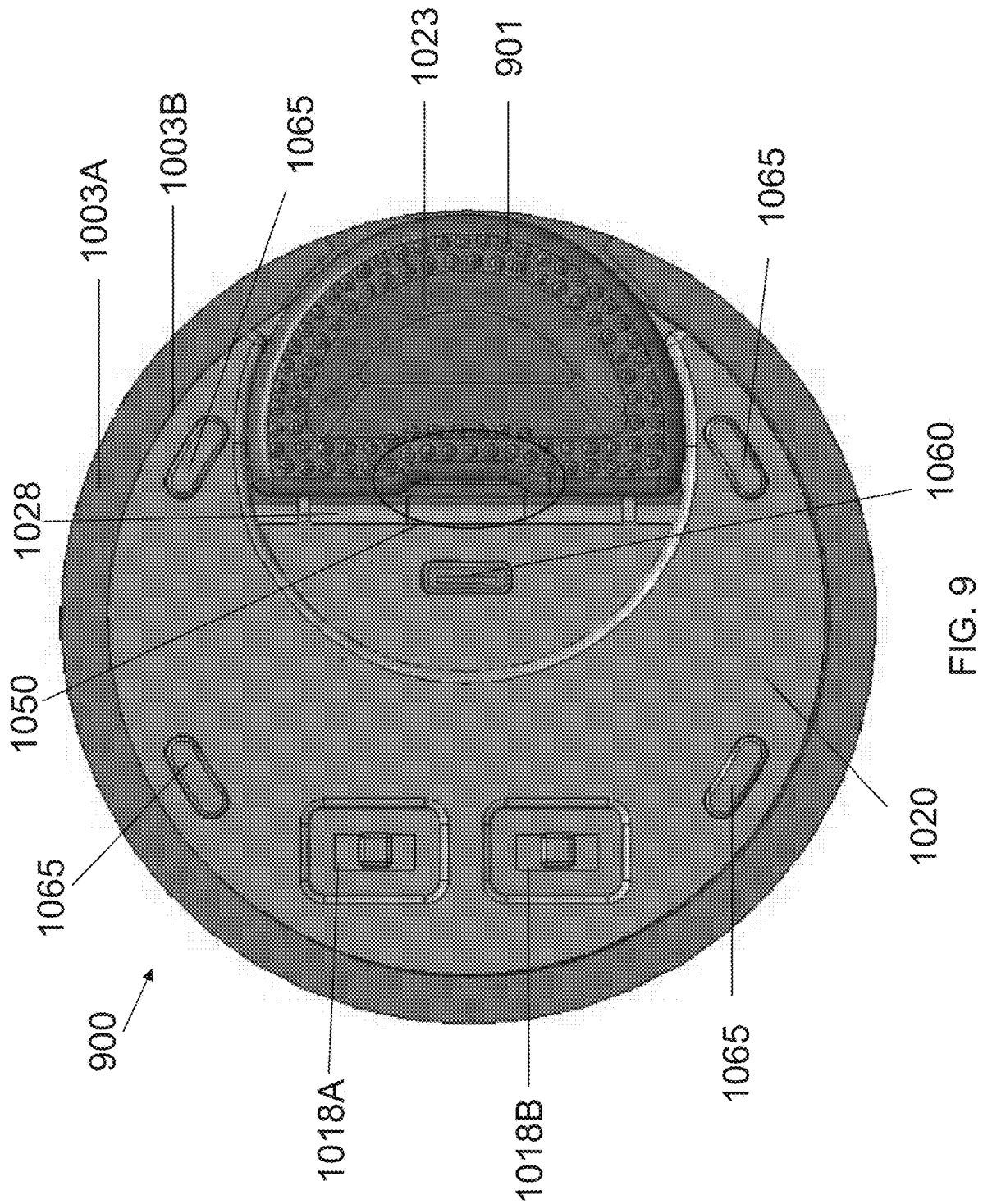
FIG. 9 illustrates a bottom view of an example electronic candle device in accordance with an embodiment of the present disclosure.

FIG. 9 illustrates a bottom view of the electronic candle device 800 in accordance with an embodiment of the present disclosure. As shown, the electronic candle device 800 includes the fragrance container 423 coupled to a mounting base 1020 disposed within the outer shell 1003A. Similar to the mounting base 420, the mounting base 1020 includes a top base 1027 (not shown) and a main body 1028 as discussed in greater details in FIGS. 10-11. As shown, the main body 1028 of the mounting base 1020 has a limiting protrusion 1050 on the sidewall facing the fragrance container 423. The part of the fragrance container 1023 facing the main body 1028 includes a groove that matches the limiting protrusion 1050. Alternatively, or in addition, the main body 1028 of the mounting base 1020 has a limiting groove on the sidewall while the part of the fragrance container 1023 facing the main body 1028 includes a protrusion that matches the limiting groove. The limiting protrusion 1050/groove and the corresponding groove/protrusion ensure that the fragrance container 1023 is securely connected to the mounting base 1020 and prevent the fragrance container 1023 from shifting left or right from mounting base 1020. As shown, a plurality of small circular features 901 are added at the bottom of the fragrance container 1023 to provide stability and improve contact with the surface upon which the electronic candle device 800 is positioned.

The electronic candle device 800 includes an inner shell 1003B between outer shell 1003A and the mounting base 1020. The inner shell 1003B can be made of any suitable materials such as plastic, paraffin, glass, metal, ceramic, crystal, polymers, or any combination thereof. The inner shell 1003B includes an open section on a side of the inner shell 1003B extending upward from the bottom of the inner shell 1003B. The open section of the inner shell 1003B is at least the same size as the open section 930 of the outer shell 1003B. In some examples, the open section of the inner shell 1003B is greater than the open section of the outer shell 1003A.

The electronic candle device 800 includes a number of support legs 1065 at the bottom of the mounting base 1020. The number of support legs 1065 is configured to allow the electronic candle device to be positioned on a flat surface. As shown, the electronic candle device 800 includes four spaced-apart support legs 1065 at the bottom of the mounting base 1020. However, the number of the support legs 1065 is not limiting and can be any suitable integer. In some embodiments, the number of support legs 1065 is not enclosed by the outer shell 1003A or the inner shell 1003B. In some embodiments, the number of support legs 1065 is positioned beneath the outer shell 1003A and the inner shell 1003B.

The electronic candle device 800 includes a first toggle switch 940 and a second toggle switch 950 at the bottom of the mounting base 1020 to control operations of the electronic candle device 800. As shown, the first toggle switch 1018A and the second toggle switch 1018B each include three positions. In some embodiments, the first toggle switch 1018A is the same as, or functionally substantially similar to the first toggle switch 418A, and the second toggle switch 1018B is the same as, or functionally substantially similar to the second toggle switch 418B. In some embodiments, the first toggle switch 1018A is the same as, or functionally substantially similar to the second toggle switch 418B, and the second toggle switch 1018B is the same as, or functionally substantially similar to the first toggle switch 418A.

The electronic candle device 800 comprises an electric receptacle 1060 for connection to a power supply to charge a battery 1057 (not shown in FIG. 9). In some embodiments, the receptacle 1060 may include a magnet that attracts another magnet that is embedded as part of a power cord or an external power supply. When connection to a power source is needed, for example, to charge the battery 1057 of the electronic candle device 800, the power cord can be moved to the vicinity of the receptacle 1060. The attractive force of the magnets can then assist in moving the power cord to properly mate with the receptacle 1060. When the battery 1057 is fully charged or the electronic candle device 800 is not in use, the power cord can be disconnected. The magnetic member of the receptacle 1060 can be a magnet or an electromagnet that interacts with the magnet on the power cord, or may be made of a material, such as iron, that allows the magnet of the power cord to be attracted to, and thus move toward, the receptacle 1060. In some embodiments, the receptable 1060 may be a regular receptacle without including a magnet.

Figure 10:
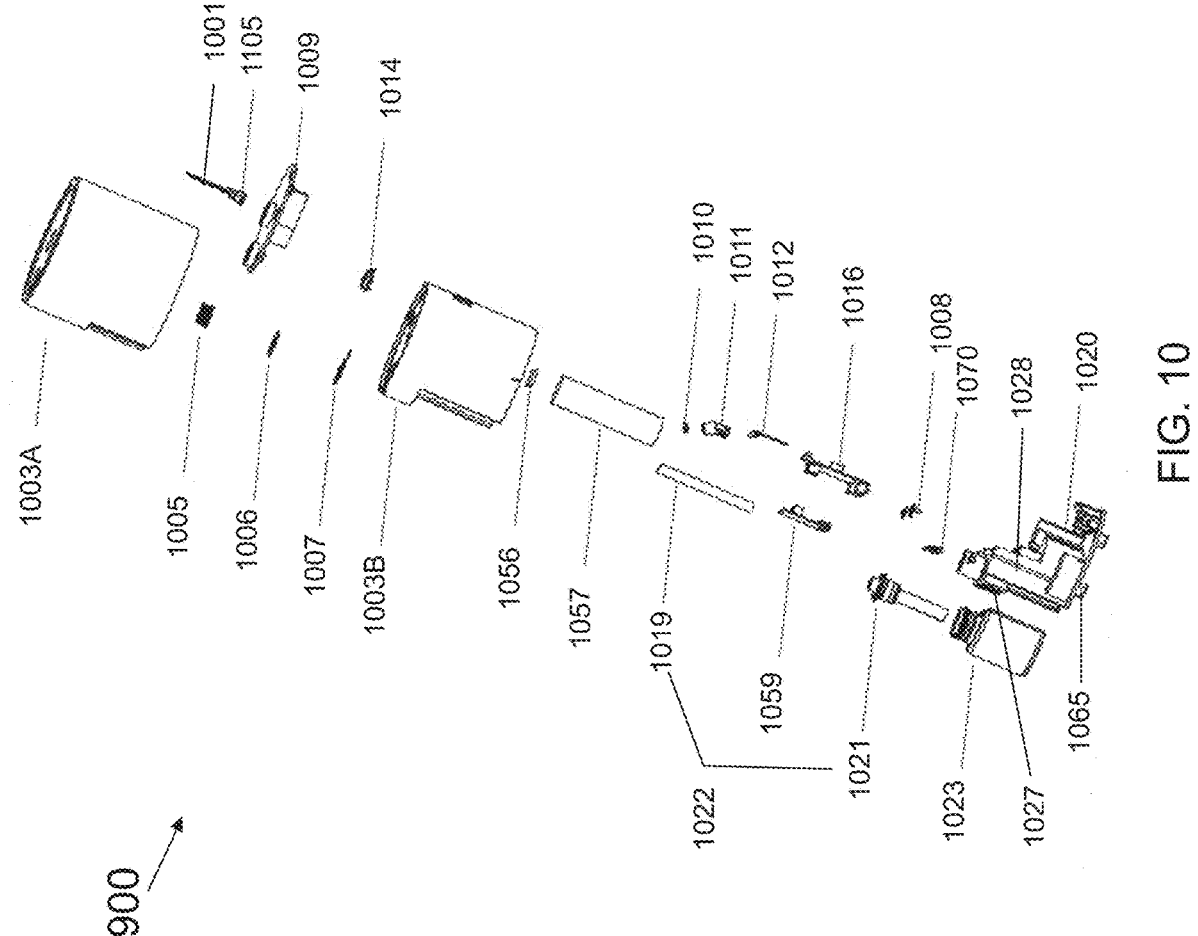
FIG. 10 illustrates an exploded view of an example electronic candle device in accordance with an embodiment of the present disclosure.

FIG. 10 illustrates an exposed view of the electronic candle device 800 in accordance with an embodiment of the present disclosure. As shown, the electronic candle device 800 includes the flame element 1001 that includes a magnet 1105 at the lower end of the flame element 1001. The electronic candle device 100 further includes the outer shell 1003A, the inner shell 1003B, a spring 1005, a ring gasket 1006, an atomizer 1007, screws 1008, a support structure 1009, a lens 1010, a lens holder 1011, one or more light-emitting elements 1012, a magnetic coil 1014, an Ethylene Vinyl Acetate (EVA) 1056, a battery 1057, a charging control circuit 1059, a control circuit 1016, a liquid suction channel 1022 including an absorptive section 1019 and a housing 1021, the mounting base 1020, the fragrance container 1023, and a light-transmitting part 1070. The mounting base 1020 includes the top base 1027, the main body 1028, support legs 1065, the first toggle switch 1018A (not shown in FIG. 10), and the second toggle switch 1018B (not shown in FIG. 10). Although not shown, the electronic candle device 800 may include a detection unit and one or more light sources that are substantially similar to the detection unit 610 and the one or more light sources 710. As discussed with relation to FIG. 11, the electronic candle device 800 may include one or more indicator light emitters 1110 to illuminate the fragrance container 1023 to cause the remaining fragrance material in the fragrance container 1023 to be visible and/or to indicate the remaining power of the battery 1057.

The control circuit 1016 is coupled to the one or more light-emitting elements 1012 and the first toggle switch 418A to control operations of the one or more light-emitting elements 1012 according to the respective position selected on the first toggle switch 1018A as discussed above. In some examples, the control circuit 1016 is also coupled to the detection unit and the one or more light sources to indicate whether the fragrance container 1023 is properly installed to the mounting base 1020. The control circuit 1016 may control the operations of the one or more indicator light emitters 1110 to illuminate the fragrance container 1023 to cause the remaining fragrance material in the fragrance container 1023 to be visible. In addition, the control circuit 1016 is coupled to the atomizer 1007 and the second toggle switch 1018B to control operations of the atomizer 1007 according to the respective position selected on the second toggle switch 1018B as discussed above. In some embodiments, the control circuit 1016 is a printing circuit board (PCB).

The charging control circuit 1059 is coupled to the receptable 1060 and the battery 1059 to charge the battery 1059. The charging control circuit 1059 may also be coupled to the one or more indicator light emitters 1110 to indicate the remaining power of the battery 1059. In some embodiments, the charging control circuit 1059 is a PCB.

Figure 11:
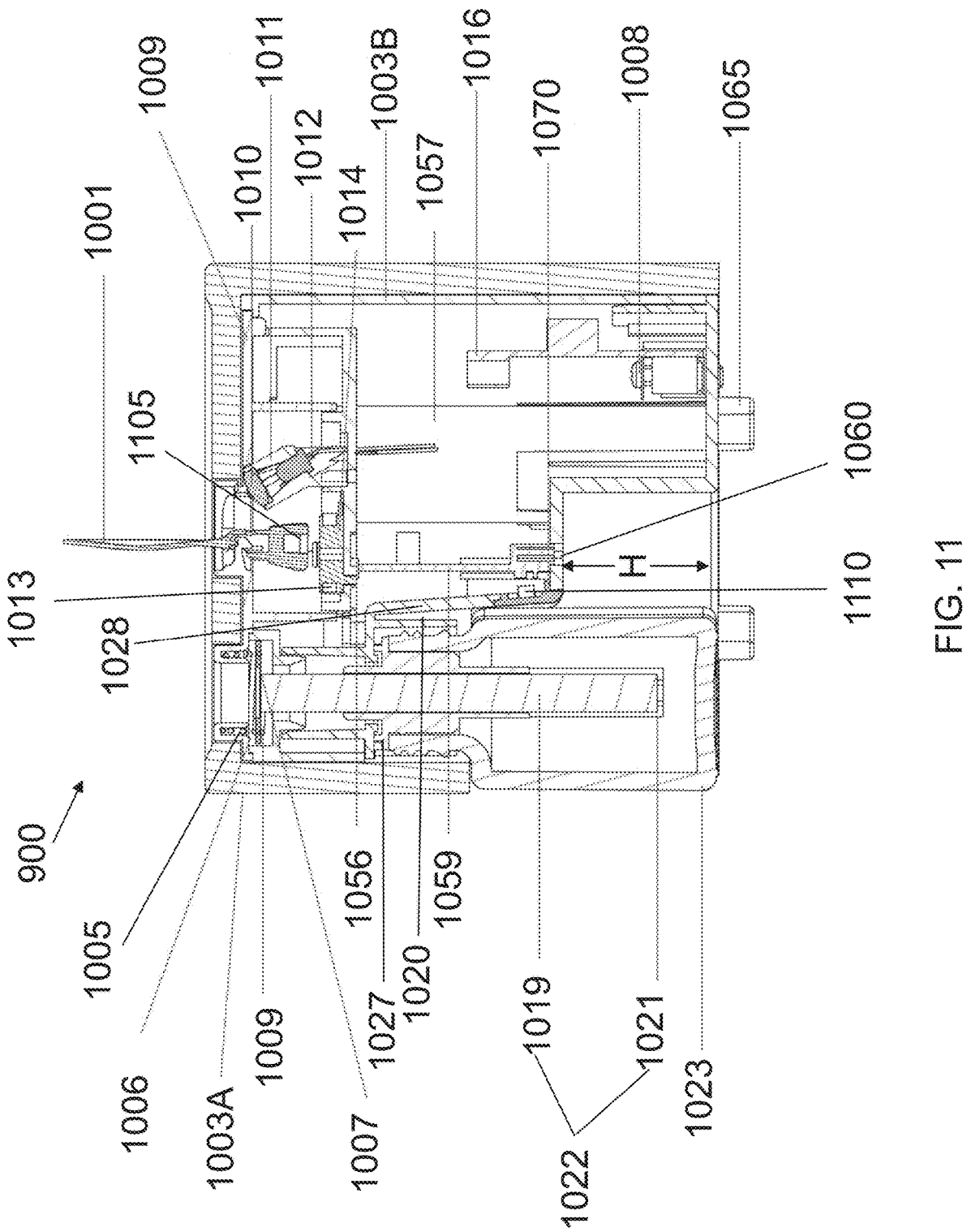
FIG. 11 illustrates a cross-sectional view of an example electronic candle device in accordance with an embodiment of the present disclosure.

FIG. 11 illustrates a cross-sectional view of the electronic candle device 800 in accordance with an embodiment of the present disclosure. As shown, the electronic candle device 800 includes the support structure 1009 between the outer shell 1003A and the inner shell 1003B. In some embodiments, the flame element 1001 is coupled to the support structure 1009 through a coupler (not shown). In some examples, the coupler has one end that is fixedly coupled to the support structure 1009 and the other end movably coupled to the flame element 1001. In some examples, the coupler has one end that is movably coupled to the support structure 1009 and the other end fixedly or movably coupled to the flame element 1001. In some embodiments, the flame element 1001 can be either fixedly or movably coupled to a wire that is similar to the wire 402 and positioned across the first opening 1001 and passing through a hole in the flame element 1001 to support the flame element 1001. In some embodiments, a hook bracket may be provided in the electronic candle device 800 to support the flame element 1001.

In some embodiments, the flame element 1001 includes a magnet 1105 at the lower end of the flame element 1001. The electronic candle device 800 includes the magnetic coil 1014 positioned below the flame element 1001. The magnetic coil 1014 is coupled to the control circuit 1016 to after the generated magnetic field, thereby driving the movement of the flame element 1001 to simulate the movement of a real flame. In some embodiments, the magnetic coil 1014 can be secured in the coil holder 1013. In some examples, the oil holder 1013 is part of the inner shell 1003B. In some embodiments, the magnetic coil 1014 and the coil holder 1013 are substantially similar to the magnetic coil 414 and the coil holder 413, respectively. In some embodiments, the flame element 1001 is driven by an air flow produced by a fan or from the outside of the electronic candle device 800.

The electronic candle device 800 includes the one or more light-emitting elements 1012 that emit light onto the flame element 1001. The one or more light-emitting elements 1012 may include one or more LEDs. In some embodiments, the one or more light-emitting elements 412 are the same as, or substantially similar to the one or more light-emitting elements 412. In some embodiments, the one or more light-emitting elements 1012 emit lights of different colors. In some embodiments, the one or more light-emitting elements 1012 are coupled to the lens holder 1011 at an upward inclined angle so that the light emitted by the one or more light-emitting elements 1012 can illuminate on the upper part of the flame element 1001. In some embodiments, the one or more light-emitting elements 1012 are coupled to the lens holder 1011 at an upward inclined angle so that the light emitted by the one or more light-emitting elements 1012 can illuminate on the upper part of the flame element 1001. In some embodiments, the lens holder 1011 is substantially similar to the light-emitting element holder 411. In some embodiments, at least part of the one or more light-emitting elements 1012 is movable with respect to the lens holder 1011 and the flame element 1001. The lens holder 1011 provides the lens 1010 positioned between the one or more light-emitting elements 1012 and the flame element 1001 to direct and focus the light emitted from the one or more light-emitting elements 1012 to the flame element 1001. The angle of the light illuminated by the one or more light-emitting elements 1012, the relative movement between the flame element 401 and the one or more light-emitting elements 1012, and/or the combination of colors of the lights from the one or more light-emitting elements 1012 form an effect that simulates a real flame.

As discussed above, the mounting base 1020 includes the top base 1027 and the main body 1028. In some embodiments, the top base 1027 of the mounting base 1020 is formed as a clamp to allow the top end of the fragrance container 1023 to be securely clamped to the mounting base 1020. In some embodiments, the top base 1027 includes a mounting hole into which the top end of the fragrance container 1023 is inserted and securely clamped. In some embodiments, the liquid suction channel 1022, the absorptive section 1019, the housing 1021, and the fragrance container 1023 are the same as, or substantially similar to the liquid suction channel 422, the absorptive section 419, the housing 421, and the fragrance container 423, respectively. As shown, the liquid suction channel 1022 is inserted into the fragrance container 1023 through the opening of the fragrance container 1023. The lower end of the liquid suction channel 1022 extends into the fragrance container 1023, and the upper end extends outside of the fragrance container 1023. The angle of the liquid suction channel 1022 with respect to a central axis of the fragrance container 1023 can be adjusted. The arrangement of the liquid absorption channel 1022 is configured to maximize the amount of fragrance drawn from the fragrance container 1023 and to control the direction in which the fragrance is directed from the fragrance container 1023. In some embodiments, the processes of inserting the fragrance container 1023 to the mounting base 1020 and of removing the fragrance container 1023 from the mounting base 1020 are substantially similar to those of inserting the fragrance container 423 to the mounting base 420 and of removing the fragrance container 423 from the mounting base 420 as described with respect to FIG. 7. The open section 930 provides an unobstructed space on one side of the mounting base 1020 to facilitate insertion of the fragrance container 1023 into the mounting base 1020 and removal of the fragrance container 1023 from the mounting base 1020.

The liquid suction channel 1022 includes the housing 1021 and the absorptive section 1019 disposed within the housing 1021. The absorptive section 1019 includes an absorbent material capable of absorbing liquid, such as cotton or woven felt, so as to deliver the fragrance material in the fragrance container 1023 from the lower end of the absorptive section 1019 to the upper end of the absorptive section 1019 due to the capillary action. In some embodiment, the housing 1021 includes at least one opening formed on a sidewall of the housing at the lower end of the housing 1021. In addition or alternatively, the housing 1021 includes an opening formed on the bottom of the lower end of the housing 1021. The housing 1021 is made of waterproof material, such as oiled paper or plastic wrap, to prevent excessive loss of fragrance during movement of the fragrance from the lower end of the absorptive section 1019 to the upper end of the absorptive section 1019. The absorptive section 1019 is at least as long as the housing 1021. In some examples, the absorptive section 1019 is longer than the housing 1021.

The atomizer 1007 is positioned in the shell 403 and in proximity to the upper end of the absorptive section 1019 of the liquid suction channel 1022. In some embodiment, the atomizer 1007 is in contact with the upper end of the absorptive section 1019. As shown in FIG. 11, the atomizer 1007 has one side above and supported by the inner shell 1003B and the other side in touch with the ring gasket 1006 that is positioned above the atomizer 1007. Additionally, the spring 1005 is positioned above the ring gasket 1006 with one end of the spring 1005 coupled to the support structure 1009 (and beneath the second opening 920) and the other end of the spring 1005 coupled to the ring gasket 1006.

In some embodiments, the spring 1005 is positioned beneath the atomizer 1007 with one end of the spring attached to the inner shell 1003B and a second end of the spring coupled to the atomizer 1007. The ring gasket 1006 is positioned above the atomizer 1007 and between the atomizer 1007 and the support structure 1009. Such arrangement allows the atomizer 1007 to be secured inside the outer shell 1003A. In some embodiments, the atomizer 1007, the ring gasket 1006, and the spring 1005 are the same as, or substantially similar to the atomizer 407, the ring gasket 406, and the spring 405, respectively.

The atomizer 1007 is coupled to the control circuit 1016 and can convert the fragrance material, which is delivered from the lower end to the upper end of the absorptive section 1019, from a liquid state into droplets. This generates a spray that is disseminated into the ambient environment through the second opening 920 on the top section of the outer shell 1003A. In some embodiments, the atomizer 1007 includes a plurality of holes in the center area that allows the droplets to pass through the atomizer 1007. In some embodiments, the upper end of the absorptive section 1019 is in contact with at least a portion of the holes in the atomizer 1007.

As shown in FIG. 11, the top base 1027 protrudes from one side of the main body 1028 to be coupled with the fragrance container 1023 such that the fragrance container 1023 is arranged side by side with the main body 1028. Additionally, or alternatively, the fragrance container 1023 can be connected to the main body 1028 of the mounting base 1020. In some examples, the bottom of the top base 1027 is perpendicular with the sidewall of the main body 1028 to form an inverted L shape. In some embodiments, the sidewall of the main body 1028 is coupled to the top base 1027 and extends vertically downward. Different from the sidewall of the main body 428 that extends vertically downward to the bottom of the mounting base 420, the sidewall of the main body 1028 does not extend downward to the bottom of the mounting base 1020. As shown, there is a vertical distance H between the bottom of the sidewall of the main body 1028 and the bottom of the mounting base 1020. Accordingly, a cavity is formed between the sidewall of the main body 1028 and the bottom of the mounting base 1020. In some embodiments, the vertical distance, H is less than half the height of both the inner shell 1003B and the outer shell 1003A. As shown, the receptacle 1060 is positioned at the bottom of the sidewall of the main body 1028. The cavity provides a space for the power cord to be connected to the receptacle 1060 to charge the electronic candle device 800 and to be routed below the bottom of the mounting base 1028 when the electronic candle device 800 is positioned on a flat surface through the support legs 1065.

The light-transmitting part 1070 is positioned on the sidewall of the main body 1028 and behind the fragrance container 1023 when the fragrance container is installed to the mounting base 1020. In some embodiments, the light-transmitting part 1070 is positioned at the bottom center of the sidewall of the main body 1028. The light-transmitting part 1070 can be made of materials that allows a light to pass through it. The light-transmitting part 1070 may have any suitable shape, including but not limited to any one of a rectangle, a square, trapezoid, a rhombus, an ellipse, a water droplet, or a combination thereof.

As shown, the electronic candle device 800 includes one or more indicator light emitters 1110 positioned inside the main body 1028 of the mounting base 1020 and behind the light-transmitting part 1070 facing the fragrance container 1023. The one or more indicator light emitter 1110 can illuminate the fragrance container 1023 through the light-transmitting part 1070 so that the remaining fragrance material in the fragrance container 1023 is visible to the users. For example, the fragrance container 1023 can be made of transparent or semi-transparent materials. The one or more indicator light emitters 1110 are connected to the control circuit 1016 that can cause the one or more indicator light emitters 1110 to illuminate the body of the fragrance container 1023 in the dark environment such that the amount of the fragrance material remained in the fragrance container 1023 is visible to the user of the electronic candle device 800. In some embodiments, the one or more indicator light emitter 1110 may include one or more LEDs.

In addition, or alternatively, the one or more indicator light emitters 1110 are connected to the charging control circuit 1059 that can cause the one or more indicator light emitters 1110 to indicate a remaining power of the battery 1057 in the electronic candle device 800. For example, when the battery 1057 of the electronic candle device 800 is running low on power and just begins to charge, the charging control circuit 1059 causes the one or more indicator light emitters 1110 to emit a light of a first color. When the battery 1057 is charged to a certain level (for example, 50%), the light is changed to a second color. When the battery 1057 is fully charged, the light is changed to third color. As such, the color of light emitted by the one or more indicator light emitters 1110 may indicate the power level of the battery 1057. For example, the first color is red, the second color is yellow, and the third color is white. In another example, when the battery 1057 is not being charged and the electronic candle device 800 is in normal operation mode, the charging control circuit 1059 may cause the one or more indicator light emitters 1110 to emit lights in different colors when the battery 1057 is at different power levels. In some embodiments, the charging control circuit 1059 may cause the one or more indicator light emitters 1110 to emit lights only when the power level of the battery 1057 has dropped to a certain level, for example, 20% so that the users are informed to either charge the battery 1057 or replace the battery 1057 with a new one.

Figure 12:
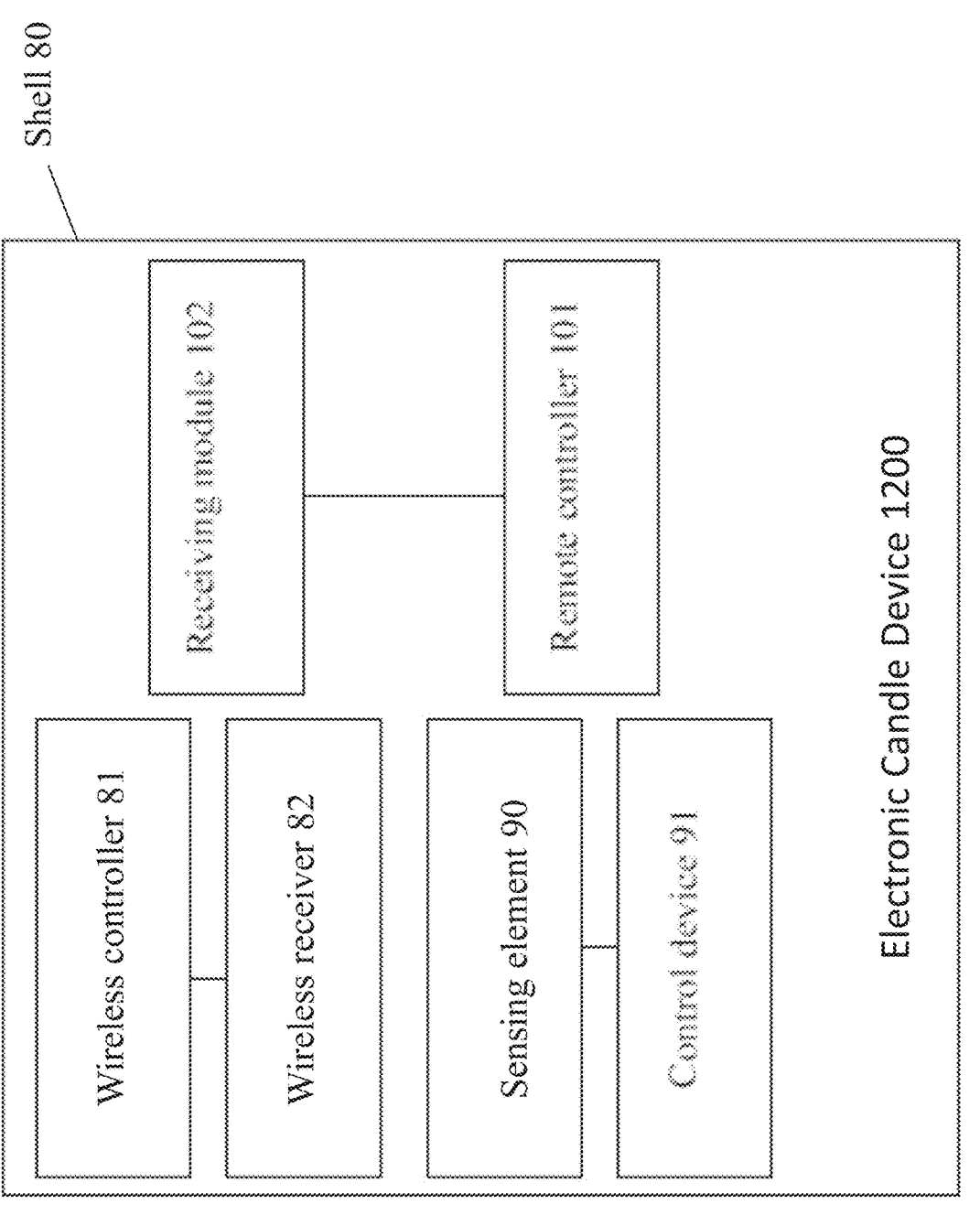
FIG. 12 is a schematic diagram of some of the components of an example electronic candle device in accordance with an embodiment of the present disclosure.

FIG. 12 is schematic diagrams of some of the components of electronic candle device 1200 in accordance with an embodiment of the present disclosure. The electronic candle device 1200 may be the electronic candle device 100 or the electronic candle device 800. The electronic candle device 1200 includes a wireless controller 81 and a wireless receiver 82. The wireless controller 81 and the wireless receiver 82 may operate using any wireless protocol or technology. For example, when the wireless controller 81 and the wireless receiver 82 use the Wireless Fidelity (WiFi) technology, they are also referred to as a WiFi controller 81 and the wireless receiver 82, respectively. Specifically, the wireless controller 81 is used to control one or more operations of the electronic candle device 1200. The wireless receiver 82 is used to receive wireless signals and convert the received wireless signals into electric signals as inputs into the wireless controller 81. The signals provided over a wireless network can be generated by a mobile terminal that runs an application to issue commands and instructions to the wireless receiver 82, which receives those instructions via the wireless network, converts the instructions into an electric signal, and communicates them to the wireless controller 81. The wireless controller 81 controls, in turn, an operation of the electronic candle device 1200, such as to turn-on, turn-off, activate different modes of operation, or set timers. The application on the mobile terminal can also display information regarding the operational state of the electronic candle device 1200. The mobile terminal can, for example, be a cell phone, a tablet computer, or a laptop computer.

The electronic candle device 1200 includes a control device 91 and a sensing element 90. The control device 91 is used to control an operation of the electronic candle device 1200. The sensing element is used to receive an external input and convert the received external input into an electric signal, which is provided to the control device 91. The sensing element can for example receive an external signal or stimulus, such as a sound, air flow and pressure, a touch, or a movement, and convert the external signal into an electric signal that causes the control device 91 to control an operation of the electronic candle device 1200. For example, a user may, via voice control or pressure control, control various operations of the electronic candle device 1200, such as to turn it on and off, to set different operational modes, or set timer operations. Alternatively, or additionally, the user can blow (or direct an airflow using a fan) to the sensing element to cause the electronic scented candle's flame to be "blown out" or extinguished by the fan. In this scenario, the control device 91 receives the signals associated with the detection of the blow or air flow and can extinguish the "flame" of the electronic candle device 1200. At the same time, the control device 91 can control a smoke device to produce smoke to simulate the smoke produced when a real candle is extinguished.

In some embodiments, the sensing element 90 includes a capacitive sensor. When a user touches the electronic candle device 1200, the capacitance of the capacitive sensor changes, and the change in capacitance is converted to an electric signal that is input into the control device 91. In such embodiments, a user may control an operation of the electronic candle device 1200 by touching it. In particular, the user can touch or knock on the shell 80, which causes the capacitance of the capacitive sensor to change and produce an electric signal. The control device 91 receives the electric signal and controls, according to the signal, an operation of the electronic candle device 1200, such as to turn in on or off, activate different modes of operation, or set timer values. For example, the user can knock on the shell 80 once to turn on the electronic candle 1200 and knock the shell 80 again to turn off the electronic candle device 1200. Knocking the shell 80 continuously can activate the timers, and a touch that persists for a long time (e.g., for more than a predetermined duration) can activate the setting of an operational modes. The control of the electronic candle device 1200 by means of touching has the following advantages, including allowing the electronic candle device 1200 to maintain an appearance of a natural candle (by eliminating the need for implementation of visible switches or knobs) while allowing for activating different operational modes by simply touching an outside area of the electronic candle device 1200. In some embodiments, a control switch is provided at the bottom of the electronic candle device 1200, which forces the user to pick up the electronic candle device 1200 to control its operation. The capacitive sensor may be disposed at different positions on the electronic candle devices 1200. In some embodiments, the capacitive sensor is disposed on the external surface of the electronic candle device 1200, and the surface of the capacitive sensor is provided with a non-metal layer. The material of the non-metal layer can the same as the material of the shell 80, such as wax or plastic to ensure the consistency and elegance of the electronic candle device 1200. Alternatively, or in addition to the capacitive sensor, the sensing element 90 includes a pressure sensor that can be used to sense pressure or force that is excreted on the candle device and convert the pressure to an electric signal for input to the control device 91.

In some embodiments, the sensing element 90 includes a sound sensor that is used to respond to a sound wave and convert the sound wave into an electric signal that is provided to the control device 91. A user may control an operation of the electronic scented candle 1200 by using voice. For example, the sound sensor receives a sound wave (e.g., a word or a phrase uttered by the user) and converts the sound wave to an electric signal that is used by control device 91 to control an operation of the electronic candle device 1200, such as to turn on/off the candle or set timers. In one example, the user can activate the electronic candle device 1200 using a voice command, such as ""Hello Scent" or "Hello Candle," or initiate a particular operation of the electronic candle device 1200 via a voice command, such as "Turn on the scent." In response, the sound sensor captures the sound wave associated with the voice comment and controls the operation of the atomizer (for example, the atomizer 407 or 1007) to turn on the scent feature of the electronic candle device 1200. In another example, a user can inquire: "Check the current state of the scent", in response to which, the control device 91 can provide feedback regarding the current scent-releasing rate of the fragrance. In yet another example, the user can ask: "Set ascent", in response to which the control device 91 can adjust the current scent-releasing level of the fragrance. For example, the user may directly say "high scent," "medium scent," or "low scent" to request the appropriate levels of scent release. In still another example, the user tells the electronic candle device 1200 "Turn off the scent," in response to which the control device 91 turns off the atomizer of the electronic candle device 1200.

It should be understood that the above description regarding voice control of the scent feature is one example of various voice control operations that can be implemented in accordance with the disclosed embodiments. In some example embodiments, the sensing element 90 is a microphone. The microphone can be disposed above the fragrance container 423, 1023 or disposed on top surface of the shell 80. In other examples, the microphone can be disposed at a position to the right or left of the flame element (e.g., the flame element 401,1001) of the electronic candle device 1200. In such a configuration, the flame element can hide the microphone from plain view, which makes the appearance of the electronic candle device 1200 closer to a real candle. Moreover, a sound wave can be immediately captured by the microphone, thereby ensuring the reliability and speed of actions that are initiated by the voice commands. In some embodiments, the control device 91 of the electronic candle device 1200 can recognize and react to a plurality of languages, such as Chinese, English, Japanese, Korean, etc. In some embodiments, during the voice interaction between a user and the electronic candle device 1200, the electronic candle device 1200 may provide feedback to the user via voice. In such embodiments, the electronic candle device 1200 includes a power amplifier circuit and a loudspeaker therein to enable such feedback.

In some embodiments, the electronic candle device 1200 comprises a remote controller 101 that is coupled to a receiving module 102. The receiving module 102 receives commands and signals from a remote control (not shown), converts them to electrical signals and communicates them to the remote controller 101 to control various operations of the electronic scented candle 300, such as to turn on or off the electronic candle device 1200. The mode of signal transmission by the remote control may be carried out via infrared, Bluetooth, high-frequency module, and other wireless transmission technologies. In some embodiments, the electronic candle device 1200 includes a notch near the receiving module 102. Alternatively, the receiving module 102 includes a shell that is made of a transparent or translucent material to allow the receiving module 102 to receive signals from all angles. In some embodiments, the remote control can have 10 touch keys: Touch Key 1 turns the product on/off; Touch Keys 2 to 4 can correspond to high, medium and low fragrance concentration (high-speed volatilization of fragrance (high), mid-speed volatilization of fragrance (mid), and low-speed volatilization of fragrance (low)), respectively; Touch Keys 5 to 7 can correspond to different durations of heating device operation, e.g., 120 min, 180 min, 240 min working duration, respectively; Touch Keys 8 to 10 can correspond to different durations for operation of the light-emitting devices, e.g., 6 hours, 8 hours, and 10 hours, respectively. A user may set the duration for the atomizer (e.g., the atomizer 407, 1007) and/or the one or more light-emitting elements (e.g., the one or more light-emitting elements 412, 1012) according to specific requirements.

In the present disclosure, the terms such as "first" and "second" are only for the purpose of illustration and they do not indicate or imply any relative importance. The term "a plurality of" means two or more, unless indicated otherwise explicitly. The term "connected" may refer to "connected directly" or "connected via an intermediate component." In the above description, it is to be noted that the terms indicating directions or positional relations, such as "up" and "down," indicates directions or positional relations as shown in the figures. They are for the purpose of simplifying description of the present disclosure, and do not indicate or imply that the device or unit in question should always be construed to have a particular direction or operate in a particular direction.

Some of the components or modules that are described in connection with the disclosed embodiments can be implemented as hardware, software, or combinations thereof. For example, a hardware implementation can include discrete analog and/or digital components that are, for example, integrated as part of a printed circuit board. Alternatively, or additionally, the disclosed components or modules can be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application.

Some of the embodiments related to operations such as processing of signals or performing certain tasks and processes, described herein are described in the general context of methods or processes, which may be implemented at least in-part by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

The foregoing is merely illustrative of the preferred embodiments of the present disclosure and is not intended to limit the present disclosure. Various changes and modifications may be made by those skilled in the art. Any modifications, equivalent alternatives are improvements that are made without departing from the spirit and principles of the present disclosure are to be encompassed by the scope of the present disclosure.

Only a few examples and implementations are disclosed. Variations, modifications, and enhancements to the described examples and implementations and other implementations can be made based on what is disclosed.

EXAMPLES

Example 1. An electronic candle device, comprising: a movable flame piece resembling a real flame; a shell comprising a first opening and a second opening on a top section of the shell, wherein the first opening is configured to allow the movable flame piece to at least partially extend outwardly from the top section of the shell, and the second opening is configured to allow dissemination of a fragrance material to an outside environment of the electronic candle device; one or more light-emitting elements located inside the shell and configured to illuminate the moveable flame element; a mounting base positioned below the moveable flame element; a fragrance container removably coupled to the mounting base and configured to store the fragrance material; a liquid suction channel, wherein a first end of the liquid suction channel protruding from the fragrance container and a second end of the liquid suction channel positioned within the fragrance container and configured to draw the fragrance material from the fragrance container; and an atomizer positioned inside the shell and coupled to the first end of the liquid suction channel, the atomizer configured to convert the fragrance material from a liquid state into droplets, wherein the atomizer is coupled to the second opening to allow the droplets to reach the second opening for dissemination to the outside environment, wherein the shell comprises an open section at a side of the shell extending upward from a bottom of the shell, the open section configured to allow at least a portion of the fragrance container to be visible from an outside of the electronic candle device when the fragrance container is coupled to the mounting base, the open section providing an unobstructed space on one side of the mounting base to facilitate insertion or removal of the fragrance container into or from the mounting base.

Example 2. The electronic candle device of any one or more examples disclosed herein, comprising a plurality of spaced-apart support legs positioned below the bottom of the shell that allow the electronic candle device to be positioned on a flat surface.

Example 3. The electronic candle device of any one or more examples disclosed herein, wherein the second opening is the only opening on the top section of the shell for dissemination of the fragrance material to the outside environment of the electronic candle device.

Example 4. The electronic candle device of any one or more examples disclosed herein, wherein the atomizer is positioned in contact with the first end of the liquid suction channel.

Example 5. The electronic candle device of any one or more examples disclosed herein, wherein the atomizer comprises a plurality of holes to allow the droplets to pass through the atomizer.

Example 6. The electronic candle device of any one or more examples disclosed herein, comprising: a spring positioned in the shell, wherein a first end of the spring is attached to a support structure beneath the shell; and a ring gasket sandwiched between the atomizer and a second end of the spring and configured to secure a position of the atomizer inside the shell.

Example 7. The electronic candle device of any one or more examples disclosed herein, wherein the movable flame element is supported by a wire or a hook bracket to allow movement of the movable flame element that mimic the real flame.

Example 8. The electronic candle device of any one or more examples disclosed herein, wherein the movable flame element comprises a magnet, and wherein the electronic candle device comprises a magnetic coil positioned below the movable flame element configured to alter a magnetic field to enable the movement of the movable flame element.

Example 9. The electronic candle device of any one or more examples disclosed herein, wherein the one or more light-emitting elements are positioned to illuminate the movable flame element from within the shell at an upward inclined angle.

Example 10. The electronic candle device of any one or more examples disclosed herein, comprising a lens positioned between the one or more light-emitting elements and the movable flame element and configured to direct a light from the light-emitting elements to the movable flame element.

Example 11. The electronic candle device of any one or more examples disclosed herein, comprising a toggle switch on a bottom of the electronic candle device and configured to cause the one or more light-emitting elements to be turned on, turned off, or operate in a timer mode.

Example 12. The electronic candle device of any one or more examples disclosed herein, comprising a toggle switch coupled to the mounting base and configured to cause the atomizer to be turned off, to operate at a first frequency, and to operate at a second frequency, wherein the first frequency is different than the second frequency.

Example 13. The electronic candle device of any one or more examples disclosed herein, wherein the fragrance container is configured to hold water such that the electronic candle device is operated in a humidification mode.

Example 14. The electronic candle device of any one or more examples disclosed herein, wherein the liquid suction channel comprises a housing, the housing comprising an opening formed at least partially on a sidewall of the housing at the second end of the liquid suction channel.

Example 15. The electronic candle device of any one or more examples disclosed herein, wherein the liquid suction channel comprises an absorptive section disposed within the housing of the liquid suction channel to facilitate movement of the fragrance material through the liquid suction channel.

Example 16. The electronic candle device of any one or more examples disclosed herein, wherein the absorptive section comprises an absorbent material to allow the fragrance material to rise from the second end of the liquid suction channel to the first end of the liquid suction channel.

Example 17. The electronic candle device of any one or more examples disclosed herein, wherein the absorbent material is cotton.

Example 18. The electronic candle device of any one or more examples disclosed herein, wherein both the second opening and the top section of the shell are circular in shape, a diameter of the second opening being at least 18% of a diameter of the top section of the shell.

Example 19. The electronic candle device of any one or more examples disclosed herein, wherein a main body of the mounting base comprises a limiting protrusion, and a part of the fragrance container facing the main body comprises a groove that matches the limiting protrusion.

Example 20. The electronic candle device of any one or more examples disclosed herein, wherein a top base of the mounting base is formed as a clamp to allow a top end of the fragrance container to be securely coupled to the mounting base.

What is claimed is:

1. An electronic candle device, comprising:
a movable flame piece resembling a real flame;
a shell comprising a first opening and a second opening on a top section of the shell, wherein the first opening is configured to allow the movable flame piece to at least partially extend outwardly from the top section of the shell, and the second opening is configured to allow dissemination of a fragrance material to an outside environment of the electronic candle device;
one or more light-emitting elements located inside the shell and configured to illuminate the moveable flame element;
a mounting base positioned below the moveable flame element;
a fragrance container removably coupled to the mounting base and configured to store the fragrance material;
a liquid suction channel, wherein a first end of the liquid suction channel protruding from the fragrance container and a second end of the liquid suction channel positioned within the fragrance container and configured to draw the fragrance material from the fragrance container; and
an atomizer positioned inside the shell and coupled to the first end of the liquid suction channel, the atomizer configured to convert the fragrance material from a liquid state into droplets, wherein the atomizer is coupled to the second opening to allow the droplets to reach the second opening for dissemination to the outside environment,
wherein the shell comprises an open section at a side of the shell extending upward from a bottom of the shell, the open section configured to allow at least a portion of the fragrance container to be visible from an outside of the electronic candle device when the fragrance container is coupled to the mounting base, the open section providing an unobstructed space on one side of the mounting base to facilitate insertion or removal of the fragrance container into or from the mounting base.

2. The electronic candle device of claim 1, comprising a plurality of spaced-apart support legs positioned below the bottom of the shell that allow the electronic candle device to be positioned on a flat surface.

3. The electronic candle device of claim 1, wherein the second opening is the only opening on the top section of the shell for dissemination of the fragrance material to the outside environment of the electronic candle device.

4. The electronic candle of claim 1, wherein the atomizer is positioned in contact with the first end of the liquid suction channel.

5. The electronic candle device of claim 1, wherein the atomizer comprises a plurality of holes to allow the droplets to pass through the atomizer.

6. The electronic candle device of claim 1, comprising:
a spring positioned in the shell, wherein a first end of the spring is attached to a support structure beneath the shell; and
a ring gasket sandwiched between the atomizer and a second end of the spring and configured to secure a position of the atomizer inside the shell.

7. The electronic candle device of claim 1, wherein the movable flame element is supported by a wire or a hook bracket to allow movement of the movable flame element that mimic the real flame.

8. The electronic candle device of claim 1, wherein the movable flame element comprises a magnet, and wherein the electronic candle device comprises a magnetic coil positioned below the movable flame element configured to alter a magnetic field to enable the movement of the movable flame element.

9. The electronic candle device of claim 1, wherein the one or more light-emitting elements are positioned to illuminate the movable flame element from within the shell at an upward inclined angle.

10. The electronic candle device of claim 9, comprising a lens positioned between the one or more light-emitting elements and the movable flame element and configured to direct a light from the light-emitting elements to the movable flame element.

11. The electronic candle device of claim 1, comprising a toggle switch on a bottom of the electronic candle device and configured to cause the one or more light-emitting elements to be turned on, turned off, or operate in a timer mode.

12. The electronic candle device of claim 3, comprising a toggle switch coupled to the mounting base and configured to cause the atomizer to be turned off, to operate at a first frequency, and to operate at a second frequency, wherein the first frequency is different than the second frequency.

13. The electronic candle device of claim 1, wherein the fragrance container is configured to hold water such that the electronic candle device is operated in a humidification mode.

14. The electronic candle device of claim 1, wherein the liquid suction channel comprises a housing, the housing comprising an opening formed at least partially on a sidewall of the housing at the second end of the liquid suction channel.

15. The electronic candle device of claim 14, wherein the liquid suction channel comprises an absorptive section disposed within the housing of the liquid suction channel to facilitate movement of the fragrance material through the liquid suction channel.

16. The electronic candle device of claim 15, wherein the absorptive section comprises an absorbent material to allow the fragrance material to rise from the second end of the liquid suction channel to the first end of the liquid suction channel.

17. The electronic candle device of claim 16, wherein the absorbent material is cotton.

18. The electronic candle device of claim 1, wherein both the second opening and the top section of the shell are circular in shape, a diameter of the second opening being at least 18% of a diameter of the top section of the shell.

19. The electronic candle device of claim 1, wherein a main body of the mounting base comprises a limiting protrusion, and a part of the fragrance container facing the main body comprises a groove that matches the limiting protrusion.

20. The electronic candle device of claim 1, wherein a top base of the mounting base is formed as a clamp to allow a top end of the fragrance container to be securely coupled to the mounting base.

* * * * *